(12) United States Patent
Zawko et al.

(10) Patent No.: US 12,390,559 B2
(45) Date of Patent: Aug. 19, 2025

(54) HYDROGEL MEDIUM FOR THE STORAGE AND PRESERVATION OF TISSUE

(71) Applicant: ALAFAIR BIOSCIENCES, INC., Austin, TX (US)

(72) Inventors: Scott A. Zawko, Austin, TX (US); Sarah M. Mayes, Austin, TX (US)

(73) Assignee: ALAFAIR BIOSCIENCES, INC., Austin, TX (US)

( * ) Notice: Subject to any disclaimer, the term of this patent is extended or adjusted under 35 U.S.C. 154(b) by 0 days.

(21) Appl. No.: 18/658,011

(22) Filed: May 8, 2024

(65) Prior Publication Data
US 2024/0285830 A1    Aug. 29, 2024

Related U.S. Application Data

(63) Continuation of application No. 16/485,256, filed as application No. PCT/US2018/021384 on Mar. 7, 2018, now Pat. No. 11,980,700.

(60) Provisional application No. 62/510,977, filed on May 25, 2017, provisional application No. 62/468,451, filed on Mar. 8, 2017.

(51) Int. Cl.
| | | |
|---|---|---|
| *A61L 27/52* | (2006.01) | |
| *A61L 27/26* | (2006.01) | |
| *A61L 27/36* | (2006.01) | |

(52) U.S. Cl.
CPC ............... *A61L 27/52* (2013.01); *A61L 27/26* (2013.01); *A61L 27/3633* (2013.01)

(58) Field of Classification Search
None
See application file for complete search history.

(56) References Cited

U.S. PATENT DOCUMENTS

| | | |
|---|---|---|
| 4,141,973 A | 2/1979 | Balazs |
| 4,196,070 A | 4/1980 | Chao et al. |
| 4,818,542 A | 4/1989 | DeLuca et al. |
| 4,937,270 A | 6/1990 | Hamilton et al. |
| 5,017,229 A | 5/1991 | Burns et al. |
| 5,266,326 A | 11/1993 | Barry et al. |
| 5,395,383 A | 3/1995 | Adams et al. |
| 5,415,631 A | 5/1995 | Churinetz et al. |
| 5,531,716 A | 7/1996 | Luzio et al. |
| 5,531,735 A | 7/1996 | Thompson |
| 5,532,221 A | 7/1996 | Huang et al. |
| 5,563,186 A | 10/1996 | Thompson |
| 5,578,314 A | 11/1996 | Cochrum et al. |
| 5,618,561 A | 4/1997 | Della Valle et al. |
| 5,622,707 A | 4/1997 | Dorigatti et al. |
| 5,688,775 A | 11/1997 | Renn et al. |
| 5,714,166 A | 2/1998 | Tomalia et al. |
| 5,750,585 A | 5/1998 | Park et al. |
| 5,760,200 A | 6/1998 | Miller et al. |
| 5,795,584 A | 8/1998 | Totakura et al. |
| 5,863,551 A | 1/1999 | Woerly |
| 5,866,554 A | 2/1999 | Shalaby et al. |
| 5,874,100 A | 2/1999 | Mahoney et al. |
| 5,919,442 A | 7/1999 | Yin et al. |
| 5,925,009 A | 7/1999 | Mahoney et al. |
| 5,939,323 A | 8/1999 | Valentini et al. |
| 5,981,821 A | 11/1999 | Barikosky |
| 5,981,825 A | 11/1999 | Brekke |
| 5,984,948 A | 11/1999 | Hasson |
| 5,993,661 A | 11/1999 | Ruckenstein et al. |
| 6,007,833 A | 12/1999 | Chudzik et al. |
| 6,030,958 A | 2/2000 | Burns et al. |
| 6,060,534 A | 5/2000 | Ronan et al. |
| 6,083,930 A | 7/2000 | Roufa et al. |
| 6,096,018 A | 8/2000 | Luzio et al. |
| 6,124,273 A | 9/2000 | Drohan et al. |
| 6,133,325 A | 10/2000 | Schwartz et al. |
| 6,150,581 A | 11/2000 | Jiang et al. |
| 6,156,572 A | 12/2000 | Bellamkonda et al. |
| 6,165,201 A | 12/2000 | Sawhney et al. |
| 6,174,999 B1 | 1/2001 | Miller et al. |
| 6,184,266 B1 | 2/2001 | Ronan et al. |
| 6,235,726 B1 | 5/2001 | Burns et al. |
| 6,271,278 B1 | 8/2001 | Park et al. |
| 6,281,341 B1 | 8/2001 | Mares-Guia et al. |
| 6,294,202 B1 | 9/2001 | Burns et al. |
| 6,334,968 B1 | 1/2002 | Shapiro et al. |
| 6,368,356 B1 | 4/2002 | Zhong et al. |
| 6,372,244 B1 | 4/2002 | Antanavich et al. |
| 6,387,978 B2 | 5/2002 | Ronan et al. |
| 6,410,044 B1 | 6/2002 | Chudzik et al. |
| 6,425,918 B1 | 7/2002 | Shapiro et al. |
| 6,497,902 B1 | 12/2002 | Ma |
| 6,500,777 B1 | 12/2002 | Wiseman et al. |
| 6,511,650 B1 | 1/2003 | Eiselt et al. |

(Continued)

FOREIGN PATENT DOCUMENTS

| | | |
|---|---|---|
| CN | 108969392 A | 12/2018 |
| CN | 109294002 B | 5/2021 |

(Continued)

OTHER PUBLICATIONS

Cho, W.J., S.H. Oh, and J.H. Lee, "Alginate Film as a Novel Post-Surgical Tissue Adhesion Barrier," Journal of Biomaterials Science-Polymer Edition, 2010, 14 pages total.

(Continued)

*Primary Examiner* — Sue X Liu
*Assistant Examiner* — Ali S Saeed
(74) *Attorney, Agent, or Firm* — Trop, Pruner & Hu, P.C.

(57) ABSTRACT

An embodiment includes therapeutic compositions that include a hydrogel medium and a plurality of tissue segments dispersed within the medium. The hydrogel medium preserves and stores the tissue through processing, transport, and storage. The embodiment addresses an identified problem of preserving a tissue, whether such tissue is fresh, cryopreserved, or sterile. The therapeutic compositions may be placed on or within the body to cover and protect wounds, provide a scaffold for reconstruction, repair, or replacement, and reduce surgical complications as a result of inflammation and scar tissue formation. Other embodiments are described herein.

19 Claims, 17 Drawing Sheets

(56) References Cited

U.S. PATENT DOCUMENTS

| | | |
|---|---|---|
| 6,521,223 B1 | 2/2003 | Calias et al. |
| 6,548,081 B2 | 4/2003 | Sadozai et al. |
| 6,566,345 B2 | 5/2003 | Miller et al. |
| 6,599,526 B2 | 7/2003 | Dimitrijevich |
| 6,600,011 B2 | 7/2003 | McDonnell et al. |
| 6,608,117 B1 | 8/2003 | Gvozdic |
| 6,610,669 B1 | 8/2003 | Calias et al. |
| 6,630,167 B2 | 10/2003 | Zhang |
| 6,630,457 B1 | 10/2003 | Aeschlimann et al. |
| 6,638,917 B1 | 10/2003 | Li et al. |
| 6,642,363 B1 | 11/2003 | Mooney et al. |
| 6,653,240 B2 | 11/2003 | Crawford |
| 6,653,420 B2 | 11/2003 | Domschke et al. |
| 6,656,974 B1 | 12/2003 | Renn et al. |
| 6,693,089 B1 | 2/2004 | Li et al. |
| 6,703,041 B2 | 3/2004 | Burns et al. |
| 6,703,444 B2 | 3/2004 | Zhao et al. |
| 6,723,709 B1 | 4/2004 | Pressato et al. |
| 6,750,262 B1 | 6/2004 | Hähnle et al. |
| 6,767,928 B1 | 7/2004 | Murphy et al. |
| 6,793,675 B2 | 9/2004 | Shapiro et al. |
| 6,818,018 B1 | 11/2004 | Sawhney |
| 6,841,153 B1 | 1/2005 | Chegini et al. |
| 6,869,938 B1 | 3/2005 | Schwartz et al. |
| 6,897,271 B1 | 5/2005 | Domschke et al. |
| 6,913,765 B2 | 7/2005 | Li et al. |
| 6,924,370 B2 | 8/2005 | Chudzik et al. |
| 6,943,154 B2 | 9/2005 | Miller et al. |
| 6,960,617 B2 | 11/2005 | Omidian et al. |
| 6,977,231 B1 | 12/2005 | Matsuda |
| 6,991,652 B2 | 1/2006 | Burg |
| 7,022,313 B2 | 4/2006 | O'Connor et al. |
| 7,060,287 B1 | 6/2006 | Hubbard et al. |
| 7,083,697 B2 | 8/2006 | Dao et al. |
| 7,201,917 B2 | 4/2007 | Malaviya et al. |
| 7,235,295 B2 | 6/2007 | Laurencin et al. |
| 7,252,832 B1 | 8/2007 | Stone et al. |
| 7,265,098 B2 | 9/2007 | Miller et al. |
| 7,347,850 B2 | 3/2008 | Sawhney |
| 7,347,968 B2 | 3/2008 | Lim et al. |
| 7,347,988 B2 | 3/2008 | Hu et al. |
| 7,459,021 B2 | 12/2008 | Bukshpan |
| 7,504,286 B2 | 3/2009 | Cho |
| 7,553,903 B2 | 6/2009 | Riegel et al. |
| 7,572,894 B2 | 8/2009 | Jin et al. |
| 7,592,418 B2 | 9/2009 | Pathak et al. |
| 7,629,388 B2 | 12/2009 | Mikos et al. |
| 7,682,540 B2 | 3/2010 | Boyan et al. |
| 7,741,476 B2 | 6/2010 | Lebreton |
| 7,758,654 B2 | 7/2010 | Hoganson |
| 7,833,284 B2 | 11/2010 | Lieberman |
| 7,919,542 B2 | 4/2011 | Hudgins et al. |
| 7,968,110 B2 | 6/2011 | Hubbard |
| 7,988,992 B2 | 8/2011 | Omidian et al. |
| 7,989,505 B2 | 8/2011 | Hu et al. |
| 7,998,204 B2 | 8/2011 | Stone et al. |
| 7,998,380 B2 | 8/2011 | Turng et al. |
| 8,012,677 B2 | 9/2011 | Steen |
| 8,025,901 B2 | 9/2011 | Kao et al. |
| 8,075,908 B2 | 12/2011 | Delaney |
| 8,097,273 B2 | 1/2012 | Fukuhira et al. |
| 8,110,242 B2 | 2/2012 | Hawkins et al. |
| 8,133,840 B2 | 3/2012 | Mika et al. |
| 8,277,831 B2 | 10/2012 | Young et al. |
| 8,323,675 B2 | 12/2012 | Greenawalt |
| 8,324,184 B2 | 12/2012 | Prestwich et al. |
| 8,455,001 B2 | 6/2013 | Ito et al. |
| 8,460,695 B2 | 6/2013 | Greenawalt |
| 8,551,136 B2 | 10/2013 | Lu |
| 8,668,863 B2 | 3/2014 | Zawko et al. |
| 8,728,499 B2 | 5/2014 | Zawko et al. |
| 8,802,115 B2 | 8/2014 | Altschuler et al. |
| 8,809,301 B2 | 8/2014 | Athanasiadis et al. |
| 8,927,521 B2 | 1/2015 | Jackson |
| 8,946,194 B2 | 2/2015 | Mayes et al. |
| 9,034,357 B2 | 5/2015 | Stopek |
| 9,095,558 B2 | 8/2015 | Mayes et al. |
| 9,320,827 B2 | 4/2016 | Zawko et al. |
| 9,371,402 B2 | 6/2016 | Chen et al. |
| 9,421,221 B2 | 8/2016 | McKay et al. |
| 9,521,839 B2 | 12/2016 | Pelle Meddahi et al. |
| 9,662,424 B2 | 5/2017 | Schmidt et al. |
| 9,770,539 B2 | 9/2017 | Parakka et al. |
| 9,896,561 B2 | 2/2018 | Zawko et al. |
| 9,987,130 B2 | 6/2018 | Weber |
| 10,786,595 B2 | 9/2020 | Zimnitsky et al. |
| 10,850,011 B2 | 12/2020 | Schmidt et al. |
| 10,940,229 B2 | 3/2021 | Saito et al. |
| 11,541,075 B2 | 1/2023 | Gooding et al. |
| 2002/0131933 A1 | 9/2002 | Delmotte |
| 2003/0134132 A1 | 7/2003 | Winterton et al. |
| 2004/0091605 A1 | 5/2004 | Bayer et al. |
| 2004/0138329 A1 | 7/2004 | Hubbell et al. |
| 2004/0241436 A1 | 12/2004 | Hsieh et al. |
| 2005/0107868 A1 | 5/2005 | Nakayama et al. |
| 2005/0282148 A1 | 12/2005 | Warren et al. |
| 2006/0173394 A1 | 8/2006 | Stroock et al. |
| 2007/0015136 A1 | 1/2007 | Sanchez-Schmitz et al. |
| 2007/0026038 A1 | 2/2007 | Bayer et al. |
| 2007/0031498 A1 | 2/2007 | Zhong et al. |
| 2007/0051630 A1 | 3/2007 | Larsson et al. |
| 2007/0202084 A1 | 8/2007 | Sadozai et al. |
| 2008/0069857 A1 | 3/2008 | Yeo et al. |
| 2008/0182012 A1 | 7/2008 | Fisher et al. |
| 2008/0254091 A1 | 10/2008 | Lee et al. |
| 2008/0264793 A1 | 10/2008 | Vigh et al. |
| 2008/0292664 A1 | 11/2008 | Giammona et al. |
| 2009/0062233 A1 | 3/2009 | Ji et al. |
| 2009/0081265 A1 | 3/2009 | Peppas |
| 2009/0170973 A1 | 7/2009 | Mattiasson et al. |
| 2009/0181074 A1 | 7/2009 | Makower et al. |
| 2009/0294049 A1 | 12/2009 | Udipi et al. |
| 2010/0055158 A1 | 3/2010 | Vitaris et al. |
| 2010/0062232 A1 | 3/2010 | Schauer et al. |
| 2010/0114313 A1 | 5/2010 | Lack et al. |
| 2010/0121261 A1 | 5/2010 | Kablik et al. |
| 2010/0217403 A1 | 8/2010 | Champion et al. |
| 2010/0273667 A1 | 10/2010 | Kotov et al. |
| 2011/0008442 A1 | 1/2011 | Zawko et al. |
| 2011/0029003 A1 | 2/2011 | Lavigne et al. |
| 2011/0070204 A1 | 3/2011 | Elias |
| 2012/0039959 A1 | 2/2012 | Tessmar et al. |
| 2012/0088832 A1 | 4/2012 | Mayes et al. |
| 2012/0213708 A1 | 8/2012 | Anderson et al. |
| 2012/0239063 A1 | 9/2012 | Lee |
| 2012/0244107 A1 | 9/2012 | Heckroth et al. |
| 2012/0282302 A1 | 11/2012 | McCanless et al. |
| 2013/0034592 A1 | 2/2013 | Yamamoto et al. |
| 2013/0052236 A1 | 2/2013 | Tessmar et al. |
| 2013/0095143 A1 | 4/2013 | Font Perez et al. |
| 2013/0195789 A1 | 8/2013 | Lu |
| 2013/0211320 A1 | 8/2013 | Alkhamesi et al. |
| 2013/0252921 A1 | 9/2013 | Lee et al. |
| 2013/0316007 A1 | 11/2013 | Ma et al. |
| 2014/0050705 A1 | 2/2014 | Lim et al. |
| 2014/0256831 A1 | 9/2014 | Ito et al. |
| 2014/0322351 A1 | 10/2014 | Gawande et al. |
| 2015/0010490 A1 | 1/2015 | Kim et al. |
| 2015/0010636 A1 | 1/2015 | Delaney |
| 2015/0064143 A1 | 3/2015 | Lee et al. |
| 2015/0290327 A1 | 10/2015 | Zenobi-Wong et al. |
| 2015/0320915 A1 | 11/2015 | Schmidt et al. |
| 2016/0243281 A1 | 8/2016 | Leach |
| 2016/0249603 A1 | 9/2016 | Suryan |
| 2016/0325006 A1 | 11/2016 | Laukkanen et al. |
| 2018/0163012 A1 | 6/2018 | Zawko et al. |
| 2021/0269638 A1 | 9/2021 | Kim et al. |
| 2022/0168334 A1 | 6/2022 | Dowling |

(56) References Cited

U.S. PATENT DOCUMENTS

| | | | |
|---|---|---|---|
| 2023/0095832 A1 | 3/2023 | Ng | |
| 2023/0101687 A1 | 3/2023 | Traverso et al. | |

FOREIGN PATENT DOCUMENTS

| | | |
|---|---|---|
| CN | 113813448 B | 12/2022 |
| CN | 116019973 A | 4/2023 |
| CN | 114984300 B | 8/2023 |
| EP | 1806367 A | 9/1997 |
| EP | 1105094 A1 | 6/2001 |
| EP | 1321516 B1 | 3/2006 |
| EP | 1778144 A2 | 5/2007 |
| IN | 202011004849 A | 8/2021 |
| JP | H04235124 A | 8/1992 |
| JP | H06100468 A | 4/1994 |
| JP | 2001212224 A | 8/2001 |
| JP | 2003062057 A | 3/2003 |
| JP | 3805654 B2 | 5/2006 |
| JP | 3796165 B2 | 7/2006 |
| KR | 20020027747 A | 4/2002 |
| KR | 20020032351 A | 5/2002 |
| KR | 20030055102 A | 7/2003 |
| KR | 20120086948 A | 8/2012 |
| KR | 101495281 B1 | 2/2015 |
| KR | 101507301 B1 | 4/2015 |
| KR | 101985368 B1 | 9/2019 |
| KR | 102078334 B1 | 2/2020 |
| WO | 1997039737 A1 | 10/1997 |
| WO | 2002064192 A1 | 8/2002 |
| WO | 2002092678 A1 | 11/2002 |
| WO | 2005020849 A2 | 3/2005 |
| WO | 2009108760 A2 | 9/2009 |
| WO | 2013174661 A1 | 11/2013 |
| WO | 2014093489 A2 | 6/2014 |
| WO | 2015186101 A1 | 12/2015 |
| WO | 2018056937 A1 | 3/2018 |
| WO | 2020051920 A1 | 3/2020 |
| WO | 2022025229 A1 | 2/2022 |
| WO | 2022038213 A1 | 2/2022 |
| WO | 2022265367 A1 | 12/2022 |
| WO | 2022265368 A1 | 12/2022 |
| WO | 2023019143 A1 | 2/2023 |

OTHER PUBLICATIONS

Chang, J.-J., et al., "Electrospun anti-adhesion barrier made of chitosan alginate for reducing peritoneal adhesions," Carbohydrate Polymers, 2012, 9 pages total.

Hirasaki, Y., et al., "Development of a Novel Antiadhesive Material, Alginate Flakes, Ex Vivo and In Vivo," Surgery Today, 2011, 8 pages total.

Xu, J.B., J.P. Bartley, and R.A. Johnson, "Preparation and characterization of alginate hydrogel membranes crosslinked using a water-soluble carbodiimide," Journal of Applied Polymer Science, 2003, 7 pages total.

Oerther, S., et al., "Hyaluronate-alginate gel as a novel biomaterial: Mechanical properties and formation mechanism," 1999, Biotechnology Bioeng, pp. 206-215.

Oerther, S., et al., "High interaction alginate-hyaluronate associations by hyaluronate deacetylation for the preparation of efficient biomaterials," 2000, Biopolymers, pp. 273-281.

Ceana, H. Nezhat, et al., "Adhesion Prevention and Management," Prevention & Management of Laparoendoscopic Surgical Complications, 3rd edition, Society of Laparoendoscopic Surgeons, 2011, 11 total pages.

Zhang, Y., et al., "Thermosensitive methyl cellulose-based injectable hydrogels for post-operation anti-adhesion," Jan. 30, 2014, 8 total pages.

Wiseman, D.M., et al., "Metaanalysis of the safety and efficacy of an adhesion barrier (Interceed TC7) in laparotomy," Apr. 1999, 3 total pages.

Dania Al-Jaroudi, MD and Togas Tulandi MD et al., "Adhesion prevention in gynecologic surgery," Aug. 2005, 9 total pages.

Ten Broek, R.P., et al., "Efficacy of polyethylene glycol adhesion barrier after gynecological laparoscopic surgery: results of a randomized controlled pilot study," 2012, 7 pages total.

Ten Broek, R.P., et al., "Benefits and harms of adhesion barriers for abdominal surgery: a systematic review and meta-analysis," The Lancet, Jan. 4, 2014, 12 pages total.

Yang, B., et al., "Prevention of abdominal adhesion formation by thermosensitive PECE-hydrogel in a rat uterine horn model," Jan. 2011, 10 pages total.

Mettler, L., et al., "A safety and efficacy study of a resorbable hydrogel for reduction of post-operative adhesions following myomectomy," May 2008, 8 pages total.

Lauder, C.I., et al., "Use of a modified chitosan-dextran gel to prevent peritoneal adhesions in a porcine hemicolectomy model," Aug. 2012, 7 pages total.

Johns, D.A., et al., "Initial feasibility study of a sprayable hydrogel adhesion barrier system in patients undergoing laparoscopic ovarian surgery," Aug. 2003, 5 pages total.

Tjandra, J.J., et al., "A sprayable hydrogel adhesion barrier facilitates closure of defunctioning loop ileostomy: a randomized trial," Jun. 2008, 5 pages total.

Diamond, M.P., "Reduction of adhesions after uterine myomectomy by Seprafilm membrane (HAL-F): a blinded, prospective, randomized, multicenter clinical study; Seprafilm Adhesion Study Group," Dec. 1996, 7 pages total.

Falabella, C.A., et al., "Novel Macromolecular Crosslinking Hydrogel to Reduce Intra-Abdominal Adhesions," Journal of Surgical Research, Apr. 2010, 7 total pages.

Hill-West, J.L., et al., "Efficacy of adhesion barriers. Resorbable hydrogel, oxidized regenerated cellulose and hyaluronic acid," Mar. 1996, 5 total pages.

Becker, J.M., et al., "Prevention of postoperative abdominal adhesions by a sodium hyaluronate-based bioresorbable membrane: a prospective, randomized, double-blind multicenter study," Oct. 1996, 2 total pages.

Li, T.C., et al., "The value of an absorbable adhesion barrier, Interceed, in the prevention of adhesion reformation following microsurgical adhesiolysis," Apr. 1994, 5 total pages.

Luo, Y., et al., "Cross-linked hyaluronic acid hydrogel films: new biomaterials for drug delivery," Journal of Controlled Release, Oct. 3, 2000, 16 total pages.

Xiao Zheng Shu, et al., "In situ crosslinkable hyaluronan hydrogels for tissue engineering," Biomaterials, Mar.-Apr. 2004, 10 total pages.

Vrijland, W.W., et al., "Fewer intraperitoneal adhesions with use of hyaluronic acid-carboxymethylcellulose membrane: a randomized clinical trial," Feb. 2002, 7 total pages.

Bennett, S.L., et al., "Next-Generation HydroGel Films as Tissue Sealants and Adhesion Barriers," Nov./Dec. 2003, 7 total pages.

European Patent Office, Examination Report mailed Jul. 29, 2020 in European patent application No. 19 156 162.0, 9 pages total.

F. Shen, et al., "A Study On The Fabrication Of Porous Chitosan/Gelatin Network Scaffold For Tissue Engineering," Polymer International, 2000, 4 pages total.

K. Lindenhayn, et al., "Retention of Hyaluronic Acid in Alginate Beads: Aspects for In Vitro Cartilage Engineering," Dec. 23, 1997, 7 pages total.

"Halobarrier Gel by Anika", Anika.com, downloaded Sep. 6, 2023, https://anika.com/medical/products/surgical-solutions/#:~:text=Hyalobarrier%C2%AE%20Gel%20and%20Hyalobarrier,in%20the%20abdomino%2Dpelvic%20area.

"SUPRO Adhesion Barrier Gel", ansermedical.com, downloaded Sep. 6, 2023, https://www.ansermedical.com/products/adhesion-barrier-supro-gel.

"An Absorbable Gel for Adhesion Prevention", fziomed.com, downloaded Sep. 6, 2023, https://www.fziomed.com/products/peritoneal-surgery/.

Froelich et al. "Alginate-Based Materials Loaded with Nanoparticles in Wound Healing", Pharmaceutics, Apr. 223; 15(4): 1142, https://www.ncbi.nlm.nih.gov/pmc/articles/PMC10143535/.

(56) References Cited

OTHER PUBLICATIONS

Bovone et al. "Engineering Hydrogel Adhesion for Biomedical Applications via Chemical Design of the Junction", pubs.acs.org., ACS Biomater. Sci. Eng. 2021, 7, 9, 4048-4076, https://pubs.acs.org/doi/10.1021/acsbiomaterials.0c01677.
Andersen et al. "In Situ Gelation for Cell Immobilization and Culture in Alginate Foam Scaffolds", ncbi.nlm.nih.gov., Tissue Eng Part A., Feb. 1, 2014; 20(3-4): 600-610, https://www.ncbi.nlm.nih.gov/pmc/articles/PMC3926177/.
European Patent Office, "Communication pursuant to Article 94(3) EPC" as mailed Dec. 13, 2017 in European Patent Application 11 831 723.9.
Specogna, et al., "Dehydration, Dissolution, and Melting of Cyclodextrin Crystals," J. Phys. Chem. B 2015, 119, pp. 1433-1442.
Zhang, et al., "Ultrafine Cellulose Acetate Fibers with Nanoscale Structural Features," J. Nanosci. Nanotechnol. 2008, vol. 8, No. 9, pp. 4461-4469.
Nie, et al., "Effects of Chain Conformation and Entanglement on the Electrospinning of Pure Alginate," Biomacromolecules 2008, 9, pp. 1362-1365.
Tilley, "Crystals and Crystal Structures," John Wiley & Sons, Ltd, England, 2006, 16 pages.
Rowley, et al., "Alginate hydrogels as synthetic extracellular matrix materials," Biomaterials, Jan. 1998, 9 pages.
Bekkers, et al., "Targeted Dendrotomy Reveals Active and Passive Contributions of the Dendritic Tree to Synaptic Integration and Neuronal Output," PNAS, Jul. 3, 2007, vol. 104, No. 27, pp. 11447-11452.
Ganesh, et al, "Enzymatically Cross-linked Alginic-Hyaluronic acid Composite Hydrogels As Cell Delivery Vehicles," International Journal of Biological Macromolecules, Apr. 2013, 11 pages.
Dahlmann, J., et al, "Fully defined in situ cross-linkable alginate and hyaluronic acid hydrogels for myocardial tissue engineering," Biomaterials (Jan. 2013) 34(4):940-951.
Mohand-Kaci, et al., "Optimized Hyaluronic Acid Design and Culture Conditions for Preservation of Mesenchymal Stem Cell Properties," Tissue Engineering Part C Methods, Apr. 2013, 13 pages.
International Searching Authority, "Notification of Transmittal of the International Search Report and the Written Opinion of the International Searching Authority," mailed Sep. 10, 2019, in International application No. PCT/US2018/021384.
Badylak, "The extracellular matrix as a biologic scaffold material," Dec. 14, 2006, 7 pages.
Rogers, "Kiln Dried May Not Mean What You Think It Means", Gibson MeIlvain Company, 2022.
Kett Marketing, "Woodworking and the Importance of Moisture Content", Kett Science of Sensing, 2018.
Hsiao et al., "Astrocytes alignment and reactivity on collagen hydrogels patterned with ECM proteins". Biomaterials, vol. 39, pp. 124-130, Jan. 2015.
Poellmann et al., "Geometric microenvironment directs cell morphology on topographically patterned hydrogel substrates", Acta Biomaterialia, vol. 6, Issue 9, Sep. 2010, pp. 3514-3523.
Gulrez et al., "Hydrogels: methods of preparation, characterisation and applications", Progress in Molecular and Environmental Bioengineering—From Analysis and Modeling to Technology Applications, ISBN: 9789833072685, 2011.

HYDROGEL MEDIUM FOR THE STORAGE AND PRESERVATION OF TISSUE

CROSS-REFERENCE TO RELATED APPLICATIONS

This application is a continuation of U.S. patent application Ser. No. 16/485,256, filed Aug. 12, 2019, which is a § 371 national stage of international application PCT/US2018/021384, filed Mar. 7, 2018, which claims priority to U.S. Provisional Patent Application No. 62/468,451 filed on Mar. 8, 2017 and entitled "Hydrogel Medium for the Storage and Preservation of Tissue" and also claims priority to U.S. Provisional Patent Application No. 62/510,977 filed on May 25, 2017 and entitled "Hydrogel Medium for the Storage and Preservation of Tissue". The content of each of the above applications is hereby incorporated by reference.

FIELD OF EMBODIMENTS

Embodiments relate generally to the field of therapeutic preparations and more particularly to hydrogel-based preparations that preserve, store, or deliver tissue to a patient. Embodiments include membranes that can be placed on external and internal wounds to cover and protect the wounds, provide a scaffold for reconstruction, repair, or replacement of tissue, and reduce surgical complications as a result of inflammation and scar tissue formation.

BACKGROUND

Inflammation and scar tissue attachments, also called adhesions, are frequent complications of surgical procedures. During a surgical procedure, the tissues and organs of the body may be deliberately or inadvertently injured. These injuries prompt a wound healing response that results in inflammation and scarring. Scarring is problematic when it produces scar tissue attachments between adjacent tissues and organs that should remain unattached. Adhesions can form in any anatomical location including around the eyes, tendons, heart, spinal cord, peripheral nerves, sinus, and among the organs of the abdominal and pelvic cavities. For example, a bowel resection within the abdominal cavity may lead to scar tissue attachments between the bowels and the abdominal wall. These attachments can produce pain and discomfort for the patient, impair the functioning of the effected organs, and hinder subsequent surgeries in the same anatomical region.

BRIEF DESCRIPTION OF THE DRAWINGS

Features and advantages of embodiments of the present invention will become apparent from the appended claims, the following detailed description of one or more example embodiments, and the corresponding figures. Where considered appropriate, reference labels have been repeated among the figures to indicate corresponding or analogous elements.

FIG. 3A. The membrane was embedded with a high density of discrete tissue powder that was evenly distributed. Scale bar: 100 µm. FIG. 3B. The amnion's epithelial "cobblestone" morphology was preserved. Scale bar: 20 µm.

DETAILED DESCRIPTION

Figure 1A:
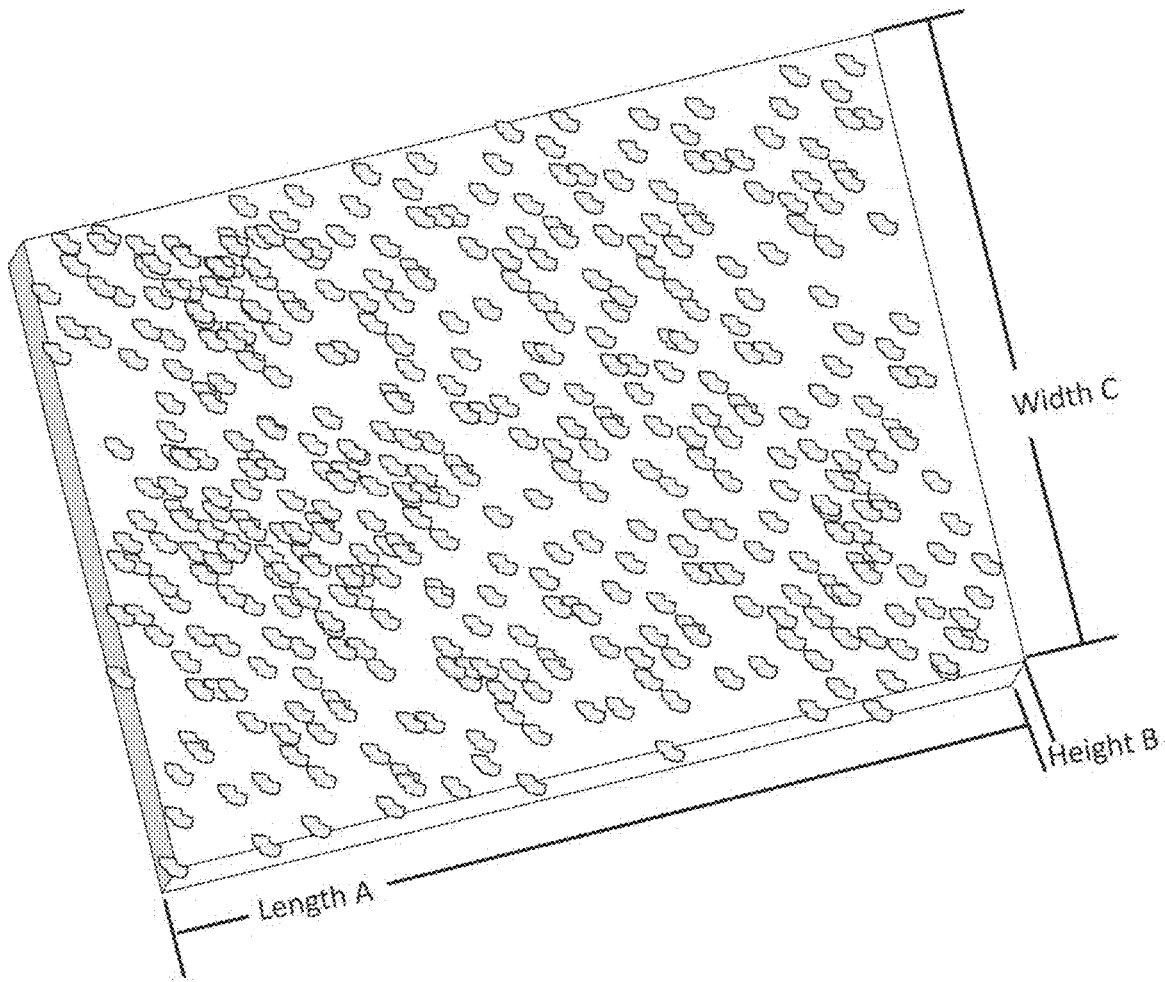
FIG. 1A. Tissue segments dispersed uniformly throughout the surface and/or bulk of the hydrogel medium in an embodiment.
Figure 1B:
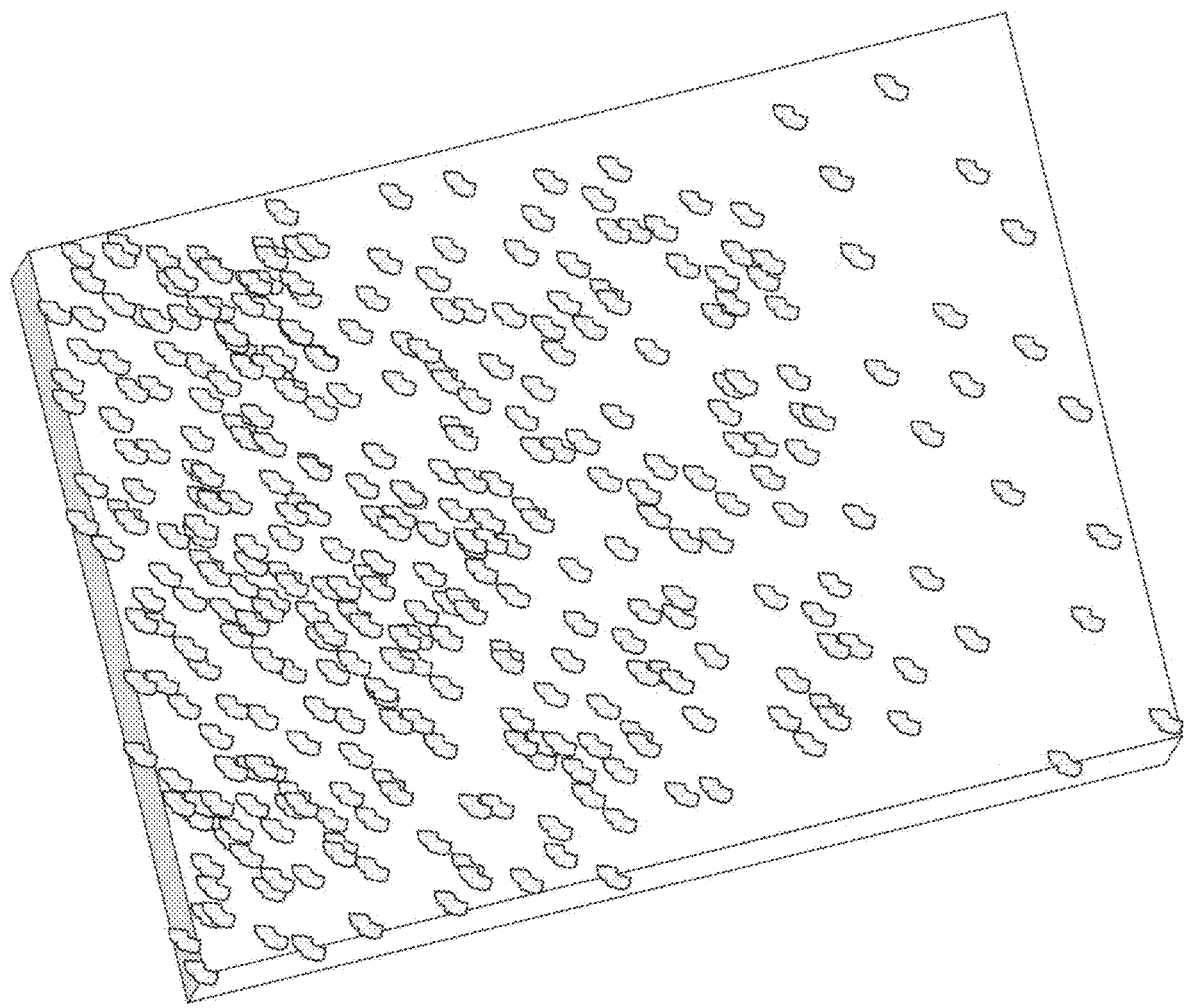
FIG. 1B. Tissue segments dispersed in a gradient on the surface and/or throughout the bulk of the hydrogel medium in an embodiment.
Figure 1C:
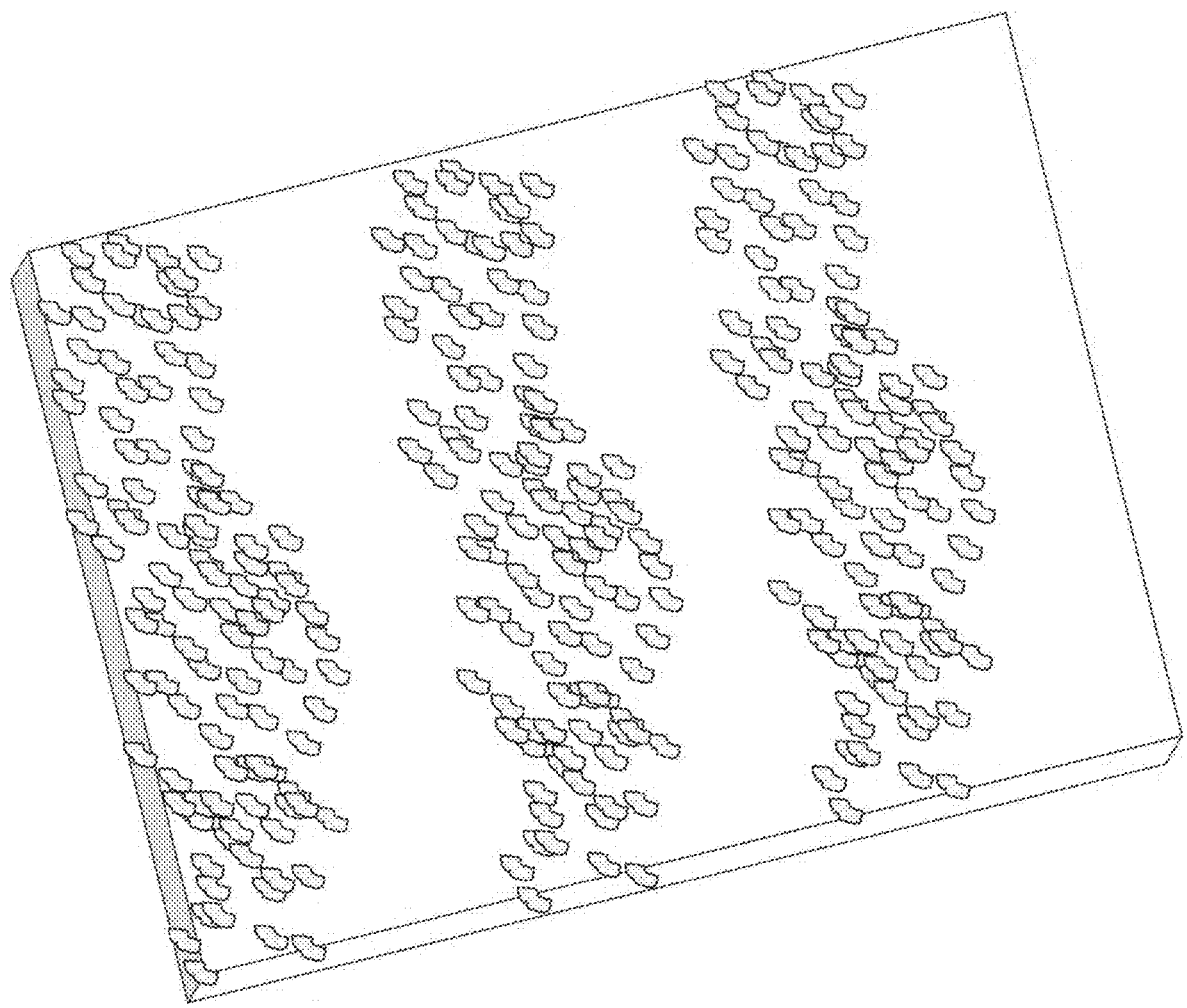
FIG. 1C. Tissue segments embedded, pressed, and/or crosslinked to the hydrogel medium in a stripe pattern in an embodiment.
Figure 1D:
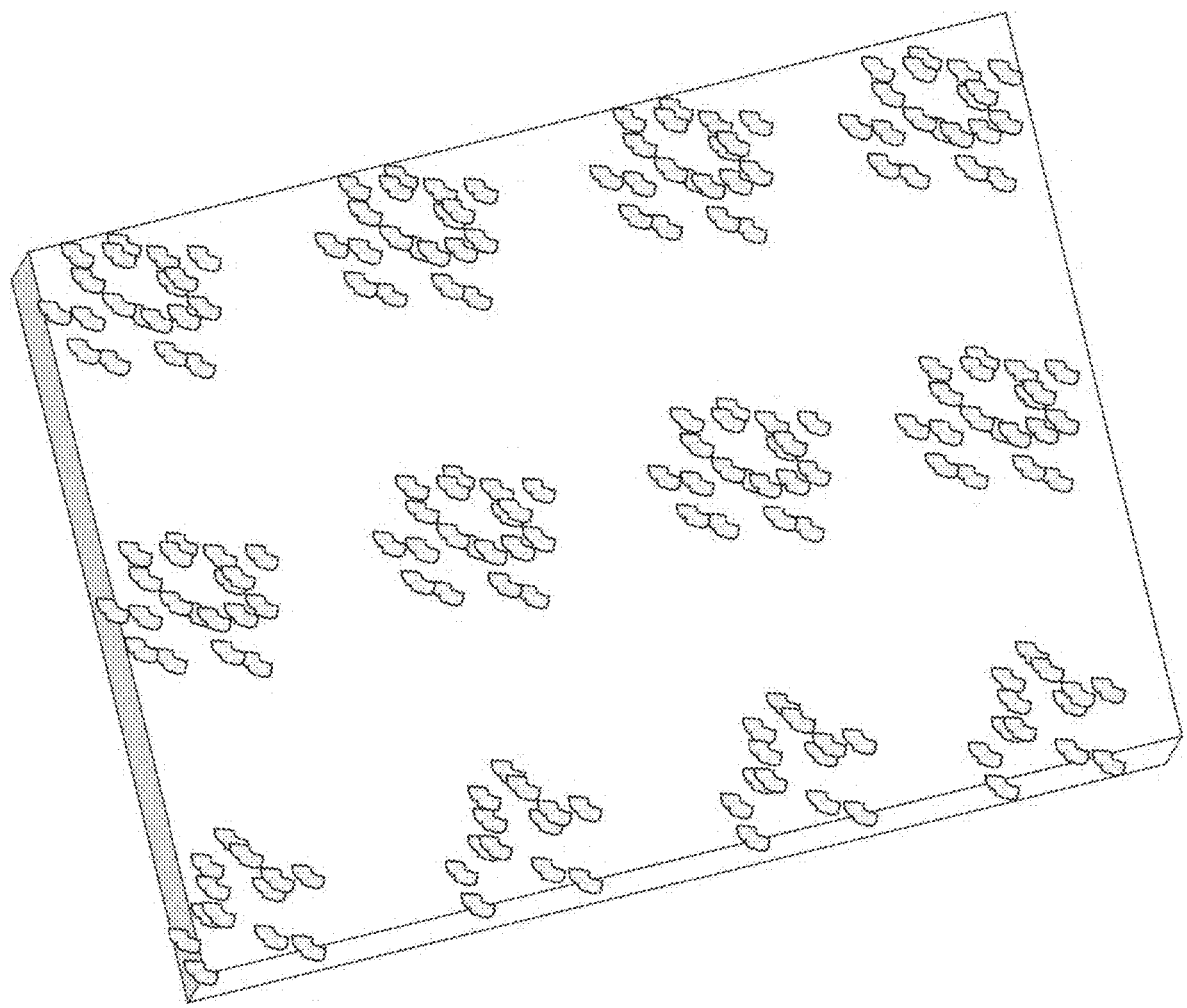
FIG. 1D. Tissue segments embedded, pressed, and/or crosslinked to the hydrogel medium in an island pattern in an embodiment.

Reference will now be made to the drawings wherein like structures may be provided with like suffix reference designations. In order to show the structures of various embodiments more clearly, the drawings included herein are diagrammatic representations of structures. Thus, the actual appearance of the fabricated structures, for example in a photomicrograph, may appear different while still incorporating the claimed structures of the illustrated embodiments. Moreover, the drawings may only show the structures useful to understand the illustrated embodiments. Additional structures known in the art may not have been included to maintain the clarity of the drawings. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner. "Connected" may indicate elements are in direct physical contact with each other and "coupled" may indicate elements co-operate or interact with each other, but they may or may not be in direct physical or electrical contact.

Tissue-based therapeutic products can be used to cover and protect wounds, provide a scaffold for reconstruction, repair, or replacement of tissue, and reduce surgical complications as a result of inflammation and scar tissue formation. However, Applicant determined processing, transport and storage of tissues between donor collection and patient treatment can reduce the sterility, efficacy, and viability of the tissue. Tissues may be damaged by dehydration, microstructural collapse, microorganismal proliferation, and oxidative damage, among other stresses experienced by the tissue. Therefore, Applicant determined there is a need for technologies that can preserve the critical properties of tissues to deliver them to patients unimpaired.

An embodiment includes any hydrogel medium with embedded tissue segments in which the tissue segments are stored and preserved through processing, transport, and storage. An embodiment includes a method of preserving and storing tissue and tissue segments within a hydrogel medium through processing, transport and storage.

An embodiment includes a membrane comprising alginate and hyaluronate and embedded segments of human or animal placental tissue. In an embodiment, the membranes can be obtained by dispersing tissue segments into an aqueous solution of alginate and hyaluronate. The solution, with dispersed tissue, can then be deposited onto a flat substrate, such as by casting into a mold, spin-coating, doctor blading, and the like, to obtain a thin film or membrane. The membranes may be stabilized through crosslinking with multivalent cations, (e.g., calcium). In an embodiment, the membranes can be further stabilized by substituting either alginate or hyaluronate with photo-reactive derivatives thereof that undergo chemical crosslinking when triggered by ultraviolet or visible light sources.

In an embodiment, the membranes can be obtained by pressing tissue or tissue segments onto the surface of a polymer membrane, for example via pneumatic press or hydraulic press, to adhere the tissue or tissue segments to the membrane without encapsulation of the tissue. In an embodiment, the polymer membrane is comprised of alginate and hyaluronate and may be either wet or dry.

In an embodiment, the membranes can be obtained by laminating tissue or tissue segments onto the surface of a polymer membrane, for example via crosslinking with glutaraldehyde, to adhere the tissue or tissue segments to the membrane. In an embodiment, the polymer membrane is comprised of alginate and hyaluronate and may be either wet or dry.

An embodiment includes a method for using the aforementioned membranes to cover and protect wounds, both external and internal. The membrane may be used in any anatomical location of the body. During a surgical procedure, the membrane may be placed between two apposing organs or tissues. The membrane may be used in both open and minimally invasive surgical procedures.

An embodiment includes a method of treating the aforementioned membrane with a stimulus, preferably a solution or gel, to modify the properties of the membrane. For example, the stimulus may enhance the tissue adherence of the membrane or increase the rate of membrane resorption within the body. Such a stimulus comprises a chelator that binds the multivalent cations stabilizing the membrane. The stimulus may be applied either immediately prior to implantation or application of the tissue or during surgical procedures following implantation or application of the membrane in or on a person's body. In an embodiment, the stimulus may be also comprised of viscosity modifiers to facilitate surgical delivery.

An embodiment is a method of treating the aforementioned membrane with a stimulus, preferably a solution or gel, to dissolve the membrane and release the dispersed tissue segments into the patient's injury. For example, the stimulus may disrupt the crosslinks within the membrane, thus solubilizing the alginate and hyaluronate components while preserving the tissue components intact. Such a stimulus comprises essentially a chelator that binds the multivalent cations stabilizing the membrane. The stimulus is applied either immediately prior to or during surgical procedures in connection with the implantation or application of the membrane to a person's body. In an embodiment the stimulus may also comprise viscosity modifiers to facilitate surgical delivery.

As used herein, sheet and membrane are used synonymously to refer to a surface area of a material with a first side, a second side, a length, a width and a thickness that is less than the length and the width.

A more detailed discussion now follows.

Clinical Application

Clinicians are seeking tissue-based wound coverings with improved handling properties, viability, and greater clinical efficacy. As discussed below, various embodiments provide a hydrogel medium that can expand the manufacturing yield of the tissue or preserve and store tissue to preserve handling properties, the extracellular matrix inherent in the tissue, and the viability of the tissues or cells present in such tissue. Embodiments may be applicable to both clinical and veterinary applications.

An embodiment includes a membranous barrier that covers and protects injured tissues by physically separating them from surrounding tissues and by providing a scaffold to facilitate soft tissue reconstruction, repair or replacement. The membranous barrier in an embodiment may comprise polymeric components and embedded tissues or tissue segments. Embodiments including membranes may be easily cut and trimmed during a surgical procedure and are convenient for covering the injured surfaces of tissues and organs. Such embodiments may be inserted into a deep or superficial wound. The membrane may be used in both open and minimally invasive surgical procedures and externally. During a surgical procedure, the membrane may be placed between two apposing organs or tissues.

An embodiment may be applied wet, which lends itself to endoscopic procedures and removes the need to desiccate the surgical field. Also, a surgical incision can be much smaller than the wetted implant.

The membrane may be used in any anatomical location of the body following a surgical procedure for which there is a risk of unwanted scarring or inflammation. For example, the abdominal cavity, peritendinous space, sinus cavity, brain, and the like. Likewise, the membrane may be placed near or around any implant that poses a risk for inflammation or scarring. An embodiment comprises an injectable viscous solution comprising polymeric components and tissue segments. The viscous solution could be used for clinical application requiring void filling and defect filling.

Components of the Hydrogel Medium

The polymeric components may be either natural or synthetic. Specific, non-limiting examples of natural polymeric components that can be used include agarose, alginate, amylopectin, amylose, carboxymethylcellulose, carrageenan, cellulose, chitin, chitosan, chondroitin sulfate, collagen, dermatan sulfate, dextran, dextran sulfate, fibronectin, gelatin, glycogen, heparan, heparan sulfate, heparin, hyaluronic acid, keratin sulfate, pectins, and starch. Specific, non-limiting examples of synthetic polymeric components that can be used include polyethylene glycol, polyvinyl alcohol, polycaprolactone, and the like. The polymeric components may be chemically modified. For example, photo-reactive derivatives may be used that undergo chemical crosslinking when triggered by ultraviolet or visible light sources.

An embodiment includes a hydrogel medium comprised of alginate and hyaluronate. An embodiment may include a membrane including only alginate and hyaluronate and little to nothing else. The proportions of each polymer within the membrane may vary with different embodiments. For example, in one embodiment the alginate component may constitute up to 95%, and no less than 10%, of the dry mass (with hyaluronate constituting the remaining portion of the film). In another embodiment, the membranes comprise no more than 75% and no less than 50% alginate by dry weight (with hyaluronate constituting the remaining portion of the film). In an embodiment, the membranes comprise between 60% and 70% alginate (with hyaluronate constituting the remaining portion of the film).

An embodiment includes a hydrogel medium comprised of alginate and carboxymethylcellulose. An embodiment may include a membrane including only alginate and carboxymethylcellulose and little to nothing else. The proportions of each polymer within the membrane may vary with different embodiments. For example, in one embodiment the alginate component may constitute up to 95%, and no less than 10%, of the dry mass (with carboxymethylcellulose constituting the remaining portion of the film). In another embodiment, the membranes comprise no more than 75% and no less than 50% alginate by dry weight (with carboxymethylcellulose constituting the remaining portion of the film). In an embodiment, the membranes comprise between 60% and 70% alginate (with carboxymethylcellulose constituting the remaining portion of the film).

In an embodiment, the alginate component may be a copolymer of mannuronate (M) units and guluronate (G) chemical units. The alginate backbone may consist of these two units arranged in repeating blocks and alternating blocks (e.g., MMMMMM, GGGGGG, and MGMGMG patterns). The proportion of M and G units in a particular alginate is dependent on, for example, the plant source from which the alginate is harvested in some embodiments. Alginates may be characterized by the proportion of M and G units. The alginate component in an embodiment may be any type of alginate including alginates with a high proportion of M units (i.e., high-M alginate), alginates with a high proportion of G units (i.e., high-G alginate) and blends of high-M and high-G alginates. In an embodiment, a "high proportion" of a unit constitutes more than 50% but in other embodiments the value may be 60%, 70%, 80%, 90%, or higher.

Alginates may be obtained in a variety of salt forms. The alginate salts of alkali metals (e.g., sodium and potassium) and magnesium are water soluble. The alginate salts of alkaline earth metals (e.g., calcium, strontium, barium) are water insoluble. Alginate can also form insoluble salts with transition metals such as iron and copper. The water insolubility of alginate salts may be due to ionic crosslinking by multivalent cations of the G-units in alginate's backbone. In an embodiment, a water soluble alginate is used to prepare solutions for film casting. After casting the alginate is converted to an insoluble salt form by ion exchange to obtain the final membrane. In an embodiment, sodium alginate is used for film casting and subsequently converted to calcium alginate after the membrane has been obtained. Calcium, an element found throughout the body, may serve as a crosslinker and is a suitable option from the point of view of biocompatibility.

Hyaluronate is an alternating polysaccharide of N-acetylglucosamine and glucuronic acid chemical units. The polymer can be obtained from, in various embodiments, both animal and bacterial sources and in a number of molecular weights. An acid form, hyaluronic acid (HA), can be obtained but has limited water solubility. Hyaluronate stocks for research and clinical use are predominantly salts, particularly sodium salts. In an embodiment, sodium hyaluronate salt is used for membrane preparation due to, for example, its commercial availability. Other salts can also be obtained, but unlike alginate, these salts are water soluble.

Hyaluronate is found throughout the connective tissues of the body particularly in the skin, cartilage, and vitreous fluid of the eye. It is an unusually large macromolecule that can reach molecular weights of up to several million. It is capable of binding to specialized proteins to form macromolecular complexes that are structural frameworks for tissue development and wound healing. The backbone of hyaluronate is highly negatively charged due to the prevalence of carboxyl functionalities. Hyaluronate is unique in the body due to the combination of high molecular weight and high charge density. These properties may make hyaluronate capable of binding to many water molecules thereby helping tissues to maintain hydration and homeostasis. Hyaluronate is biocompatible. Hyaluronate is nearly ubiquitous throughout the tissues of the body; therefore, the immune system does not recognize it as foreign. Additionally, hyaluronate is strongly associated with wound healing and particularly with scar-free wound healing and fetal tissue development.

Physical Form of the Hydrogel Medium

Hydrogels are materials that swell when exposed to excess water. At a molecular level hydrogels are comprised of a network of polymer chains that are dispersed within an aqueous medium. A feature of the hydrogel membranes of an embodiment is the crosslinks that tie together the individual polymer chains. These crosslinks allow the hydrogel to swell in water but prevent it from completely dissolving. Hydrogels tend to be biocompatible because water itself is biocompatible. Hydrogels therefore are attractive for clinical applications in which materials will come into close contact with living tissues.

In an embodiment, the hydrogel medium contains a significant proportion of water and can be classified as a hydrogel. In an embodiment, the hydrogel medium may take the form of a planar membrane, sheet, a bulk gel, or a viscous solution. In an embodiment, the planar membrane has top and bottom surfaces, a width and length, and a thickness that is less than the width and length. In an embodiment, the planar membrane's thickness ranges from 5 microns to 1 mm. The membrane may be cut to any shape such as a square, rectangle, and the like. In an embodiment, the bulk gel is a three-dimensional construct in any shape comprised of a homogeneous, non-flowable substance. The bulk gel may have many, few, or no pores. In an embodiment, the viscous solution is a flowable, thick substance with a consistency between solid and liquid.

In an embodiment, the aforementioned viscous solution is itself the hydrogel medium. In an embodiment, the viscous solution may comprise uncrosslinked hyaluronate and uncrosslinked alginate with tissue segments mixed in. The viscous solution may be flowable allowing it to be used in applications requiring an injectable composition for void and defect filling.

In an embodiment, membranes are prepared through solution casting. This requires dissolving water soluble forms of the alginate and hyaluronate in an aqueous mixture. Then a volume of the solution can be dispensed into a mold. A suitable mold can be of any shape or size. The water from the solution may be evaporated to obtain a dry thin film which can be crosslinked by a soak in an aqueous solution of a calcium salt. Crosslinking produces a hydrogel membrane that swells in water but does not dissolve. Similar techniques for obtaining cast films such as spin-casting, doctor-blading with a casting knife, extrusion and the like can produce films without the need for a water evaporation step. These films can be crosslinked with calcium without the need for drying. The membranes may be porous or non-porous; dry or wet; planar, rolled or folded.

A doctor blade is a tool used to create wet films with a defined thickness. To use the doctor blade in an embodiment one dispenses a volume of alginate/hyaluronate solution onto a substrate. Then one pulls the doctor blade over the solution to spread it into a flat film of defined thickness. The doctor blade removes excess solution thereby producing a wet film of predefined thickness coating the substrate.

In an embodiment, the hydrogel medium may comprise a bilayer or a multilayer structure with different tissue types or forms present in the layers. Fusion of layers may be accomplished through physical, ionic, or chemical bonds. An embodiment includes a multilayer hydrogel medium that may be used to deploy therapeutic tissue segments. The multilayer hydrogel may include a first layer that provides anti-inflammatory placental tissue and a second layer that provides viable cells.

In an embodiment, the hydrogel medium may be stabilized with physical, ionic, or covalent crosslinks that join together individual polymer chains. These crosslinks allow the hydrogel to swell in water but prevent it from completely dissolving. Hydrogels tend to be biocompatible because water itself is biocompatible. Hydrogels therefore are attractive for clinical applications in which materials will come into close contact with living tissues.

In an embodiment, alginate forms the framework of the membrane due to its ability to create crosslinked gels in the presence of calcium. This crosslinked framework provides mechanical stability and shape to the membrane. The hyaluronate component is entrapped within the alginate gel, which is crosslinked around it, and its release is limited by its large size compared to the pores of the alginate gel.

As used herein, "crosslinked around it" is to be construed to mean crosslinking occurs with, in this case, the hyaluronate component in place so that the component becomes entrapped once the alginate crosslinked around the component (i.e., once the alginate is mechanically stabilized due to crosslinking) thereby using the crosslinked components to physically restrain the large hyaluronate from decoupling from the alginate.

Hyaluronate is more hydrophilic than alginate and therefore hydrogel compositions with greater proportions of hyaluronate exhibit greater water swelling. When the ratio of hyaluronate to alginate is low the hyaluronate component is entirely or partially entrapped within the crosslinked alginate matrix and leaching is limited; but when the ratio of hyaluronate to alginate is high, the crosslinked alginate may be unable to retain the leachable hyaluronate component. The hyaluronate component can be leached by rinsing the membrane in water for which hyaluronate has a strong affinity. When hyaluronate is leached it leaves behind empty pores within the membrane that provide an interconnected pathway for diffusion of water. By altering the pores, and therefore the water content of the membrane, the physical properties of the membrane such as flexibility and elasticity are also altered. The leaching of hyaluronate from the membrane during manufacturing may be used as a means to advantageously modify the physical properties of the membrane. The leaching of hyaluronate may also occur in vivo as a means to deliver hyaluronate to a wound site to capitalize on hyaluronate's pro-regenerative wound healing properties.

In an embodiment, the hydrogel medium, with embedded tissue, is dried and contains little or no water. Drying of a hydrogel medium may further prolong shelf-life or facilitate sterilization methods. In an embodiment, a dried hydrogel medium may be rehydrated by dipping or immersing in a suitable aqueous solution or buffer. As used herein, "desiccation" is a more absolute form of drying.

Source of Tissue and Its Physical Form

A tissue is an aggregate of cells together with an extracellular matrix (ECM) comprised of fibrous proteins and peptides, and viscous polysaccharides and proteoglycans. A tissue may also refer to a tissue that has been decellularized to remove the cellular components while retaining the ECM components. The tissue component of an embodiment may be of any source including animal and human sources. The tissue may be fresh, viable, cadaveric or sterile. A viable tissue is one that contains living cells. If viable, the tissue may be cryopreserved with or without a cryoprotectant. The tissue may originate from any organ including, but not limited to, bone, cartilage, cornea, dura mater, embryo, fascia, heart valve, ligament, oocyte, pericardium, sclera, semen, skin, tendon, vascular graft, amniotic membrane, cardiac tissue, placenta, umbilical cord, adipose tissue, chorion, blood and bone marrow. The viable tissues may include cells such as, but not limited to, peripheral blood stem cells, somatic cells, umbilical cord blood stem cells, amniotic fluid-derived stem cells, and the like. In an embodiment, the tissues are used for autologous, allogeneic, or xenogeneic therapy, as well as for veterinary applications. In an embodiment, the tissues are stabilized via crosslinking with glutaraldehyde and the like.

The tissue component of an embodiment may be either all of a tissue, or if the tissue is too large to be contained within a hydrogel matrix, then segments of the complete tissue. For example, amnion or chorion tissue (or a combination thereof) may be subdivided into smaller segments and embedded within the hydrogel medium of an embodiment. The tissue segments of an embodiment may be in the form of bands, strands, fibers, particles, powder, drops, a net or mesh-like structure, a sheet, a film, a foil, a laminate, or a multilayer. The segments may also be square, cylindrical, spherical, or any other shape. The tissue may be obtained by any suitable means such as grinding, milling, mincing, drilling, laser cutting, meshing, automated or manual cutting, and the like. The size of tissue segments of an embodiment may range from a fine powder (0.1 microns-100 microns) up to small films (1 mm-50 mm). In an embodiment, amnion tissue segments range from 0.1 mm² to 5 mm², and most preferably from 0.2 mm² to 2 mm².

In an embodiment, the tissue segments are derived from placental tissue. Human placental tissue has been used in various surgical procedures, including skin transplantation and ocular surface disorders, for over a century. The tissue has been shown to provide good wound protection, prevent surgical adhesions, reduce pain, reduce wound dehydration, and provide anti-inflammatory and anti-microbial effects. The placenta is a fetomaternal organ consisting of a placental globe, umbilical cord, associated membranes (chorionic membrane and amniotic membrane), other gelatins, fluids, cells and extracellular material. The chorionic membrane and the amniotic membrane are attached by loose connective tissue and make up the placental sac. The innermost membrane of the placental sac is the amniotic membrane, which comes into contact with the amniotic fluid that surrounds the fetus. The amniotic membrane is avascular and lined by simple columnar epithelium overlying a basal membrane. The chorionic membrane is the outermost layer of the sac and is heavily cellularized. The placental membranes have an abundant source of collagen that provides an extracellular matrix to act as a natural scaffold for cellular attachment in the body. Collagen provides a structural tissue matrix that facilitates, among other things, cell migration and proliferation in vivo.

The amniotic membrane, when separated from the placenta, is a structural tissue that has clinical applications as a barrier and wound covering. The structural characteristics of the amnion that impact its utility to serve as a barrier are physical integrity, tensile strength and elasticity. Processing of amnion should preserve these properties. Processed segments of amnion tissue should have an average size of at least 0.5 mm to preserve the tissue's structural characteristics.

In an embodiment the tissue segments are derived from dermis. Human skin is the largest organ of the body, covering up to 20 sq. ft. Skin is a multilayer tissue comprising an outer epidermis over a deeper dermis. Dermal tissue has been used in various surgical procedures such as coverings for burns. The dermal tissue used in clinical applications may be either split thickness (i.e., the epidermis and part of the dermis) or full thickness (i.e., epidermis and dermis but excluding subcutaneous fat) depending on the severity of the burn. The surface area of a given portion of skin may be increased by meshing to increase the wound coverage of the skin-based dressing.

In an embodiment the tissue segments are derived from small intestine submucosa (SIS). Small intestine can be harvested from human (i.e., allograft) or other warm-blooded vertebrate (i.e., xenograft). The tissue comprises several layers that make up the intestinal wall. Badylak teaches that one such layer, the tunica submucosa, is a dense, irregular collagenous connective tissue that can be delaminated from the small intestine to yield SIS with excellent mechanical characteristics, non-allergenicity, and non-thrombogenicity. The SIS has applications as a vascular graft and adhesion barrier.

Dispersal of Tissue in the Hydrogel Medium by Mixing and Casting

Tissue may be introduced to the hydrogel medium by a variety of means. In an embodiment, the hydrogel medium initially comprises an uncrosslinked solution (i.e., a casting solution) of polymeric components with a viscosity suitable for film casting. In an embodiment, the tissue segments are mixed into the casting solution via vortex mixing, stirring with blades or paddles, sonic agitation and the like to result in an even dispersal of tissue. The casting solution with tissue can then be deposited onto a flat substrate using a suitable film applicator to yield a membrane with a uniform dispersal of tissue. Examples of film applicators are doctor blades, bars, brushes, sprays, and any other device that may be used to evenly spread a substance across a substrate. In an embodiment, the membrane is crosslinked by physical, ionic, or covalent means to stabilize against dissolution in aqueous media. Crosslinking may facilitate the entrapment of the tissue segments within the hydrogel medium.

Dispersal of tissue within a hydrogel medium via the method described above, wherein tissue segments are mixed into a casting solution and the casting solution is spread as a thin film, presents several challenges. First, vortex mixing, stirring with blades or paddles, sonic agitation, homogenization, and the will subject the tissue to unwanted physical stresses. Such stresses may degrade the physical integrity of the tissue or, in the case of living tissue, reduce the tissue's viability. Second, wet tissues tend to clump and aggregate rather than evenly disperse in viscous solution, which will work against an even distribution of the tissue in the resulting hydrogel. Third, spreading of a thin film using a film applicator is challenging because the tissue, prone to clumping and balling, will tend to create streaks, voids, and other unacceptable defects in the spread film. Fourth, tissue that spans the entire thickness of the film is prone to falling out entirely and creating a defect in film integrity that can lead to unwanted tearing and fragility. A fifth consideration is that when tissue is dispersed within the hydrogel medium itself, rather than on the surface of the hydrogel medium, then the hydrogel presents an unwanted barrier between the embedded tissue and the injury site. This is undesirable when the benefits of the tissue, such as scaffolding, are effective only when tissue can directly contact the injury site.

Pressing of Tissue onto the Surface of a Hydrogel Sheet

To address the problems with the mixing and casting method described above, the tissue segments can be pressed onto one or both surfaces of a pre-formed hydrogel sheet. Pressing tissue segments to a pre-formed sheet, rather than mixing into a casting solution and spreading, reduces the manipulations of the tissue and is less likely to damage the tissue during processing. Adhering the tissue segments to the surface of the sheet can have the advantage of allowing the tissue to directly contact an injury site when implanted. This direct contact, without an intervening layer of hydrogel between the tissue and patient, will support tissue incorporation. In an embodiment, tissue or tissue segments can be deposited on one side of the hydrogel medium using a pneumatic press, hydraulic press, or the like. For example, the hydrogel medium may be obtained as a thin membrane, either wet or dry, and placed onto the platen of a press. Then the tissue segments, wet or dry, can be deposited on top of the membrane. Pressure is then applied, with sufficient force and duration, to cause the tissue segments to adhere to the membrane. In an embodiment, the pressed tissue segments may be comprised of single-layer or double-layer amnion or chorion, or multiple layers of amnion and chorion with any orientation of the tissue surfaces. For example, if the tissue segments are double layer amnion, then the double layer amnion segments may be oriented such that only the epithelial surface or only the stromal surface is exposed, or oriented such that the epithelial surface is exposed on one side and the stromal surface is exposed on the other.

Figure 12:
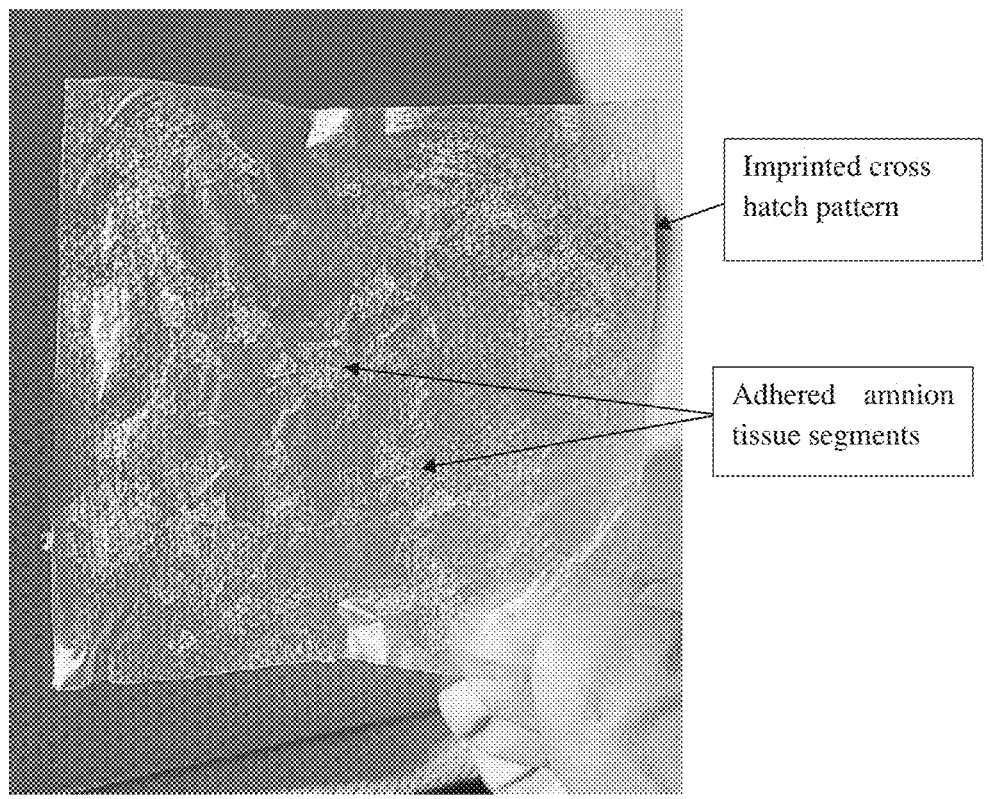
FIG. 12. Tissue segments dispersed on the surface of a planar hydrogel sheet via pressing (e.g., pneumatic or hydraulic press) in an embodiment.

Hydrogel sheets and tissue are preferably sandwiched between layers of gauze or similar material before pressing between platens. A purpose of the gauze is to prevent the tissue and hydrogel from sticking to the platens of the plate after applying pressure. If the hydrogel or tissue were to stick to the platens, then the pressed construct would separate or tear when peeled off the platen. Pressing a hydrogel and tissue in layers of gauze has the result of imprinting the gauze's texture into the hydrogel; therefore, a pressed construct can be identified by (for example) an imprinted cross-hatch pattern (FIG. 12).

In an embodiment, a patterned membrane is obtained by covering the membrane with a mask before application of the tissue segments to the exposed areas of membrane, followed by pressing. In an embodiment, tissue or tissue segments are pressed on one side of the membrane and then to the other side of the membrane. In an embodiment, multilayer constructs are created using multiple membranes and multiple layers of tissue and tissue segments.

In an embodiment, tissue or tissue segments can be laminated, layered, or adhered to one or both sides of the hydrogel medium using a crosslinking agent such as glutaraldehyde, or the like. For example, the hydrogel medium may be obtained as a thin membrane, either wet or dry, with tissue or tissue segments embedded into the hydrogel medium or pressed onto the surface. Then the multilayer construct may be exposed to a suitable crosslinking agent, such as glutaraldehyde, to cause crosslinking of the tissue or tissue segments to the hydrogel medium. In an embodiment, multilayer constructs are created using multiple membranes and multiple layers of tissue and tissue segments.

In an embodiment, the tissue segments may be deposited on only one side of the hydrogel medium. For example, the tissue segments can be spread onto a flat substrate and then the casting solution can be spread over top of the tissue segments using a suitable film applicator to yield a membrane in which the tissue is present on only the membrane's bottom surface. Crosslinking may then follow. In another embodiment, the casting solution can be deposited onto the substrate first followed by placement of tissue segments onto the exposed top surface of the membrane to yield a membrane in which the tissue is present on only the top side. In other embodiments, the tissues may be dispersed within or on the hydrogel medium either randomly or in various patterns and spatial arrangements, such as stripes, grids, islands, gradients, and the like (FIG. 1). Then the resulting membrane can be pressed to adhere the tissue and hydrogel.

Mechanisms of Storage and Preservation

There are several mechanisms by which a hydrogel medium can preserve and store an embedded tissue or tissue segments. In an embodiment, the hydrogel medium protects the tissue from damage caused by dehydration. For example, hydrated tissues have significantly different mechanical properties, such as elastic modulus, stiffness, and toughness, in comparison to dehydrated tissues. These properties can be irreversibly lost when layered tissues, such as amnion and the like, are dehydrated causing damage to the collagen fibers and extracellular matrix. A hydrogel medium can protect the embedded tissue through dehydration thereby preventing irreversible layer collapse, preventing irreversible loss of extracellular matrix microstructure such as collagen fiber integrity, and preserving delicate mechanical properties at the microscopic and macroscopic level.

In an embodiment, the hydrogel medium protects a wet tissue from unwanted loss of water. For example, the polymeric components of the hydrogel medium may be selected for their hygroscopic properties. A hydrogel medium comprised of hygroscopic components will provide beneficial humectant properties to preserve tissue hydration throughout processing, transport, and storage. The maintenance of adequate tissue hydration can preserve a tissue's native mechanical properties, extracellular matrix microstructure, and cell viability. Alginate and hyaluronate have been shown to act as humectants at a variety of temperatures up to and including room temperature. In an embodiment, hyaluronic acid is selected as a hygroscopic component of the hydrogel medium. In an embodiment, alginate is selected as a hygroscopic component of the hydrogel medium.

In an embodiment, the hydrogel medium inhibits the growth of microorganisms by lowering the activity of residual water within the tissue. Water activity can be lowered by the strong association of water for appropriately selected (i.e., hygroscopic) polymeric components. Binding of residual water has the effect of lowering the activity of the water, which for any given moisture level, leads to inhibition of the growth of microorganisms. By inhibiting the proliferation of microorganisms, the tissue's sterility can be preserved and its shelf-life prolonged.

In an embodiment, the hydrogel medium inhibits the growth of microorganisms by inhibiting protein adhesion and cellular attachment. To adhere to a surface, some bacteria must first secrete adhesive proteins that deposit onto the surface to provide an anchorage site for bacterial attachment. Appropriately selected polymeric components, such as high molecular weight polyanions, can resist the deposition of adhesive proteins by binding water so strongly that non-water molecules are excluded from the hydrogel medium.

In an embodiment, the hydrogel medium, in the form of a viscous solution, inhibits proliferation of microorganisms during processing. The mechanism of antimicrobial activity of high viscosity solutions is the promotion of microorganism flocculation. By inhibiting microorganism proliferation, the hydrogel medium can preserve the sterility of the tissue through manufacturing or processing steps.

In an embodiment, the hydrogel medium inhibits degradation of the extracellular matrix by inhibiting oxidative damage. During inflammatory processes, reactive oxygen species, such as hydroxyl radicals, and superoxide anion radicals are generated. These radicals attack the biomacromolecular components of tissues thereby reducing the molecular weight of structural proteins and carbohydrates and reducing cell viability. In an embodiment, hyaluronic acid is selected as a polymeric component of the hydrogel medium because it possesses well-known free-radical scavenging properties. Free-radicals preferentially degrade the hyaluronic acid macromolecules compared to other biomacromolecules. By suppressing free radical damage to embedded tissue segments, the hydrogel medium preserves crucial microstructural tissue properties and cell viability.

Increasing the Tissue Yield

In an embodiment, the hydrogel medium not only stores and preserves the embedded tissue but increases the effective surface area of the tissue. For example, each donor can provide only a limited amount of amnion, around 1600 $cm^2$. This amnion can be subdivided into membranes and used as a wound covering. The limited amount of amnion that is recoverable from each donor, limits the number and sizes of such wound coverings that can be obtained, and therefore increases costs to the recipient and patient. Therefore, to increase the yield from each donor amnion, an embodiment includes amnion tissue cut into segments and dispersed into a hydrogel medium, in membrane form, that greatly expands the total surface area of wound coverings can that can be obtained from one donor. An expansion of 1:2 up to 1:5, or even greater is possible. The typical size of an amnion wound covering is around 4 $in^2$ which limits its clinical applications. In an embodiment, a large amnion-based covering of 50 in$^2$, 100 in$^2$, 250 in$^2$ (i.e., the surface area of each side of the covering is 50 in$^2$, 100 in$^2$, or 250 in$^2$) or even larger is obtainable through surface area expansion and improved donor tissue yield.

Matching the Properties of the Hydrogel Medium to the Embedded Tissue

In an embodiment, the characteristics and material properties of the hydrogel medium are matched to the embedded tissue. Some such characteristics and properties are physical integrity, tensile strength, elasticity, porosity, osmotic permeability, and coefficient of friction. By embedding amnion tissue segments in a hydrogel medium with matched properties, these critical properties can be preserved even though the tissue is dispersed within the medium. In an embodiment, a hydrogel medium comprising a membrane of alginate and hyaluronate possesses an appearance, texture, feel, thickness, size, and mechanical properties comparable to that of embedded amnion tissue. The properties of amnion that are most important for preservation will depend on the intended clinical application.

Release of Tissue from the Hydrogel Medium

Discussion now turns to methods of removal of embedded tissue from the hydrogel medium. Once the tissue has been processed, transported, and stored, it may be desirable to remove the tissue from the hydrogel medium either before or after patient treatment. In an embodiment, the hydrogel medium is treated with a liquid stimulus that dissolves the hydrogel medium. Once dissolved, the hydrogel medium can be washed away to leave behind the tissue segments.

In an embodiment, the liquid stimulus comprises a sequestering solution that works by disrupting crosslinks within the hydrogel medium. Disruption of the crosslinks occurs by bonding of the sequestering agent to the crosslinking agent within the implant. For disruption to occur, in one embodiment the sequestering agent bonds more strongly to the crosslinking agent than does the crosslinkable component of the hydrogel medium. More specifically, a sequestering agent is able to sequester the crosslinking agent or ion because by doing so, the overall energy of the system is lowered. This energy lowering causes a relaxation of the hydrogel medium, reducing the mechanical integrity of the hydrogel medium. In various embodiments suitable sequestering agents are salts of organic molecules that have multiple anionic functional groups capable of bonding to a crosslinking agent (such as calcium, magnesium, cadmium, silver, zinc, silicon, oxidants, protic acids, compounds that can be metallated). Examples are the salts of citric acid, EDTA, EGTA, BAPTA, tetracycline, and phosphates.

In an embodiment, the strength of the sequestering solution is dependent on the molar concentration of the sequestering agent. For example, a solution formulated with a greater molar concentration of sequestering agent disrupts a greater number of crosslinks within the hydrogel medium.

In an embodiment, a surgeon uses the sequestering solution during any surgical procedure in which an implant, comprised of crosslinked constituents (such as calcium alginate) that can be uncrosslinked with the sequestering solution, is used to introduce tissue to a site of injury. The surgeon applies the sequestering solution by a suitable delivery device (e.g., syringe, spray, and the like) to the surface of the hydrogel medium. The sequestering solution acts quickly to disrupt the unwanted crosslinks (such as calcium). The hydrogel medium then dissolves, thus freeing the embedded tissue to directly contact the injury site.

To facilitate application of the sequestering solution to the injury site, in an embodiment the sequestering solution may be formulated with a thickening agent. The thickening agent increases the solution viscosity to produce a thick, syrupy liquid. A beneficial effect of the thickening agent is that the more viscous sequestering solution is better confined to the site of application than is a less viscous watery solution. An embodiment includes a thickening agent such as sodium hyaluronate, which is known for both its biocompatibility and solution thickening properties.

In the interests of biocompatibility in various embodiments the sequestering solution can be formulated with salts to buffer the pH or adjust the osmolarity such as those found in commonly used phosphate buffer solution.

An embodiment includes an alginate-based hydrogel medium crosslinked specifically with calcium and treated with a corresponding calcium sequestering solution. However, in other embodiments the same method can be applied to other ions as well. For example, in various embodiments alginate barriers are crosslinked with cations such as barium, strontium, copper, iron, and the like. The same sequestering agents may be used to disrupt these crosslinking agents.

In an embodiment, the hydrogel membrane and the sequestering solution may be provided within a kit. The kit would also include a delivery device suited for applying the sequestering solution to the wound site. A surgeon or other health care provider in an operating room setting would use the kit to apply the hydrogel medium and appropriate volume of sequestering solution to the wound site. This approach would afford the end user great flexibility to adjust the amount of tissue and solution volume to meet patient specific needs.

The sequestering solution may be applied to the hydrogel membrane hours, days, or weeks after the hydrogel medium's implantation at an injury site. By applying the sequestering solution at a later point in time a medical care provider can tailor the release of the tissue to match the particular needs of the patient. In an embodiment, the hydrogel membrane may be placed at a wound site for the purposes of providing a scaffold for reconstruction, repair, or replacement. The hydrogel medium could protect the implanted tissue from initial harmful inflammatory events. After the time period for inflammation has passed the preserving effects of the hydrogel medium are no longer needed; therefore, the sequestering solution may be injected into the wound site to completely solubilize the hydrogel medium. This action would have as its purpose elimination of the hydrogel from the wound site thus precluding an unwanted foreign body response. The sequestering solution can be introduced by a needle and syringe penetrating through the surrounding tissue or can be introduced by minimally invasive surgical means.

In an embodiment, the sequestering solution may be applied to the hydrogel membrane before application to an injury site. For example, the tissue could be released from the hydrogel membrane to allow the tissue to undergo further manufacturing, processing, or clinical preparation.

In an embodiment, the hydrogel medium may comprise bioresorbable polymers that need no external stimulus to slowly solubilize and release embedded tissue. In an embodiment, a hydrogel medium comprising uncrosslinked alginate and hyaluronate contain embedded amnion segments. This hydrogel medium is uncrosslinked and therefore will resolubilize in the patient's body fluids at the injury site. In an embodiment, the hydrogel medium comprises alginate crosslinked with calcium. Over time, the calcium crosslinks are displaced by sodium ions endogenous to the injury site resulting in a slow release of the embedded tissue. In an embodiment, a hydrogel medium comprising non-covalently crosslinked polyvinyl alcohol is embedded with amnion tissue segments. Over time, polyvinyl alcohol resolubilizes and releases the embedded tissue segments at a site of injury.

The following examples pertain to further embodiments.

Example 1

Figure 2:
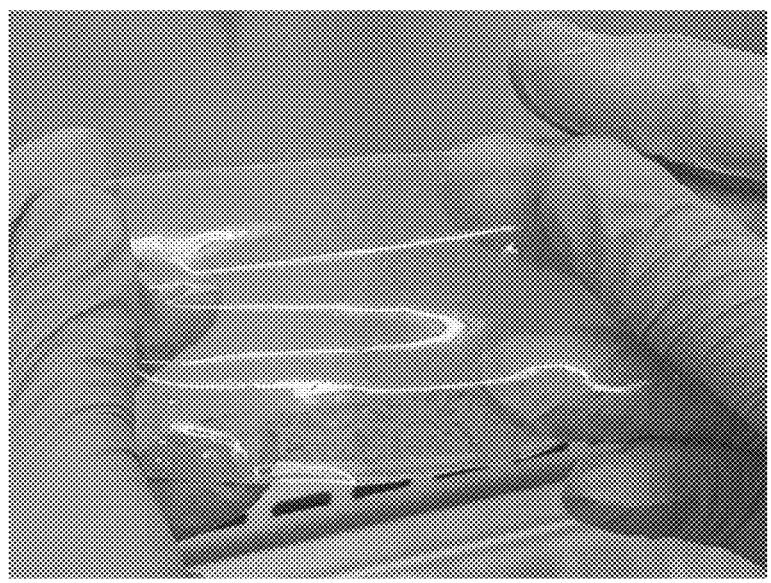
FIG. 2. Hydrogel medium with embedded amnion tissue in an embodiment.
Figure 3A:
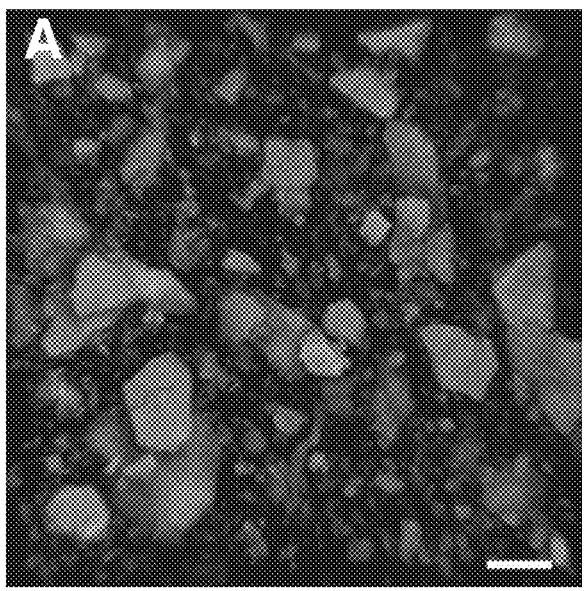
FIGS. 3A and 3B. Tissue powder embedded in a hydrogel medium imaged and imaged via confocal fluorescence microscopy.
Figure 3B:
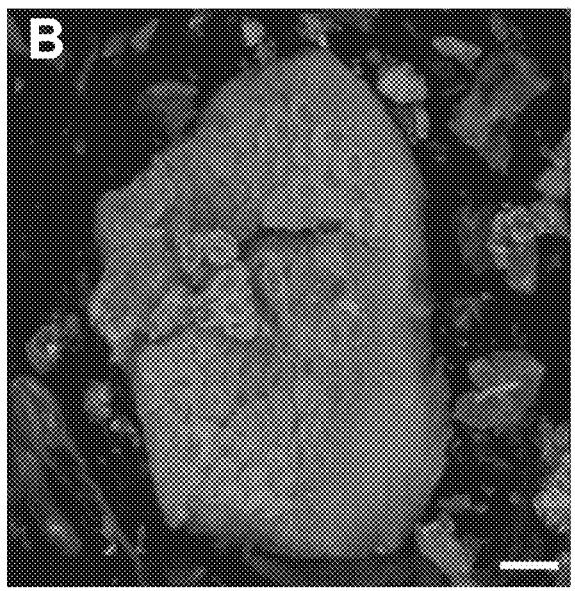

This example illustrates an embodiment in which amnion tissue is evenly dispersed throughout a hydrogel medium comprising alginate and hyaluronate. A batch of a viscous solution was prepared by dissolving alginate powder and hyaluronate powder into water with agitation. Amnion tissue was prepared via cryomilling to yield a powder measuring 0.1 to 100 microns in size. This amnion powder was mixed with cryoprotectant to form a slurry. The slurry and the aforementioned viscous solution were then mixed in a volume ratio of 1:1 in a conical tube and placed on a vortex mixer to ensure even dispersal of the tissue. After vortexing, the mixture was deposited onto paper substrates using a stainless steel film applicator and crosslinked via immersion in an aqueous calcium chloride solution. The resulting translucent membranes measured 5 cm×10 cm, were 0.25 mm in thickness, and were stable to unwanted dissolution in water. No unwanted clumping or aggregation of the tissue powder was observed (FIG. 2). Even dispersal of the tissue throughout the crosslinked membrane was confirmed by staining the tissue with 5-([4,6-Dichlorotriazin-2-yl]amino) fluorescein hydrochloride. The stained tissue was imaged via confocal fluorescence to confirm preservation of the tissue's epithelial "cobblestone" morphology (FIG. 3).

Example 2

Figure 4:
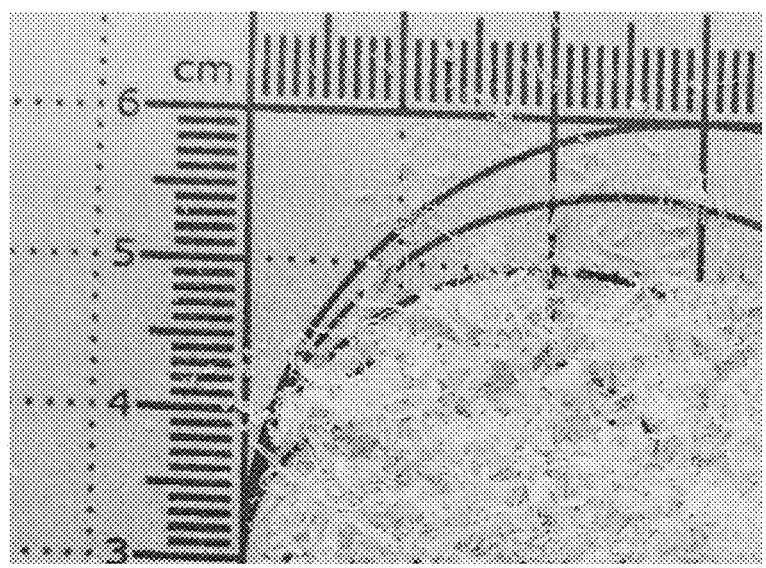
FIG. 4. Dry tissue segments of donor amnion of sizes up to 1 mm2 produced by grinding in a tissue grinder in an embodiment.
Figure 5:
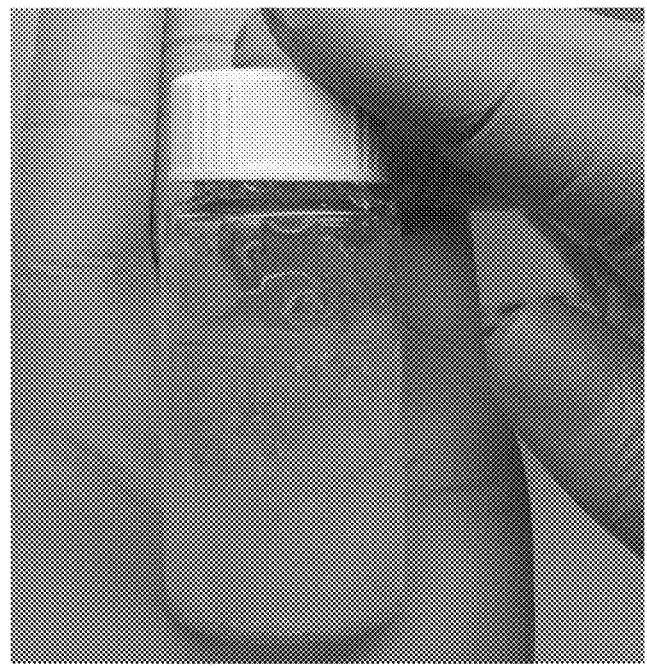
FIG. 5. A flowable slurry of amnion tissue in a viscous solution containing alginate and hyaluronate in an embodiment.
Figure 6:
FIG. 6. One-fifth of a donor amnion was cut up into segments, mixed into a casting solution and spread into the hydrogel membranes depicted. The total surface area of the membranes was equivalent to the surface area of the entire donor amnion. Therefore, a 5-fold increase in surface area was achieved by cutting amnion and dispersing into a hydrogel.

This example illustrates an embodiment in which the surface area of amnion tissue was dramatically increased by storage within a hydrogel medium. A batch of viscous solution was prepared by dissolving alginate powder and hyaluronate powder into water with agitation. Amnion tissue was prepared by drying and grinding to yield small segments measuring no larger than 1 mm$^2$ (FIG. 4). A volume of the viscous solution was added to one-fifth of the amnion segments, drop by drop, until a flowable slurry was obtained (FIG. 5). The slurry was vigorously agitated by vortex mixing. The slurry was then deposited as a thin membrane on a paper substrate using a film applicator and crosslinked via immersion in an aqueous calcium chloride solution. This method yielded a total membrane surface area of ~3200 cm$^2$ from just ~650 cm$^2$ of donor amnion. This increase in surface area represented a near 5-fold increase in the amount of material (FIG. 6).

Example 3

Figure 7:
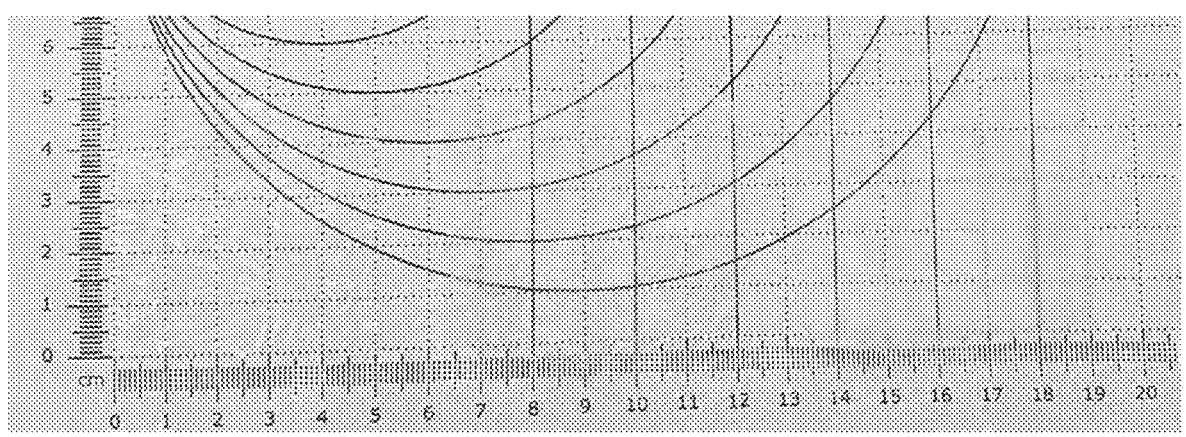
FIG. 7. Side-by-side comparison of the membrane (left), amnion (middle), and membrane with embedded tissue segments (right).
Figure 8A:
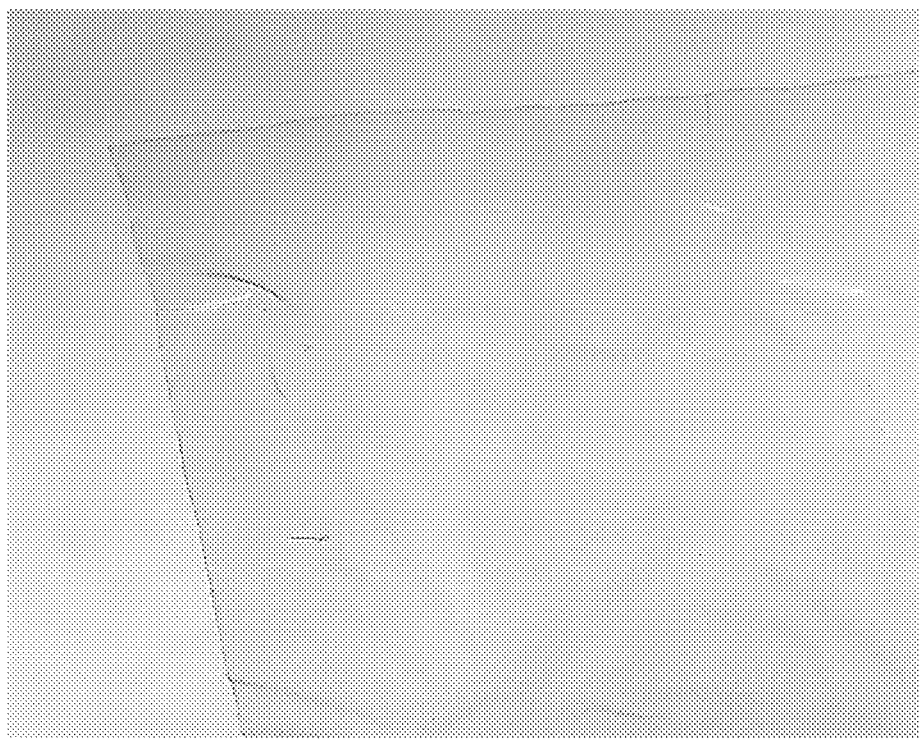
FIG. 8A. Close up view of a hydrogel membrane without embedded tissue in an embodiment.
Figure 8B:
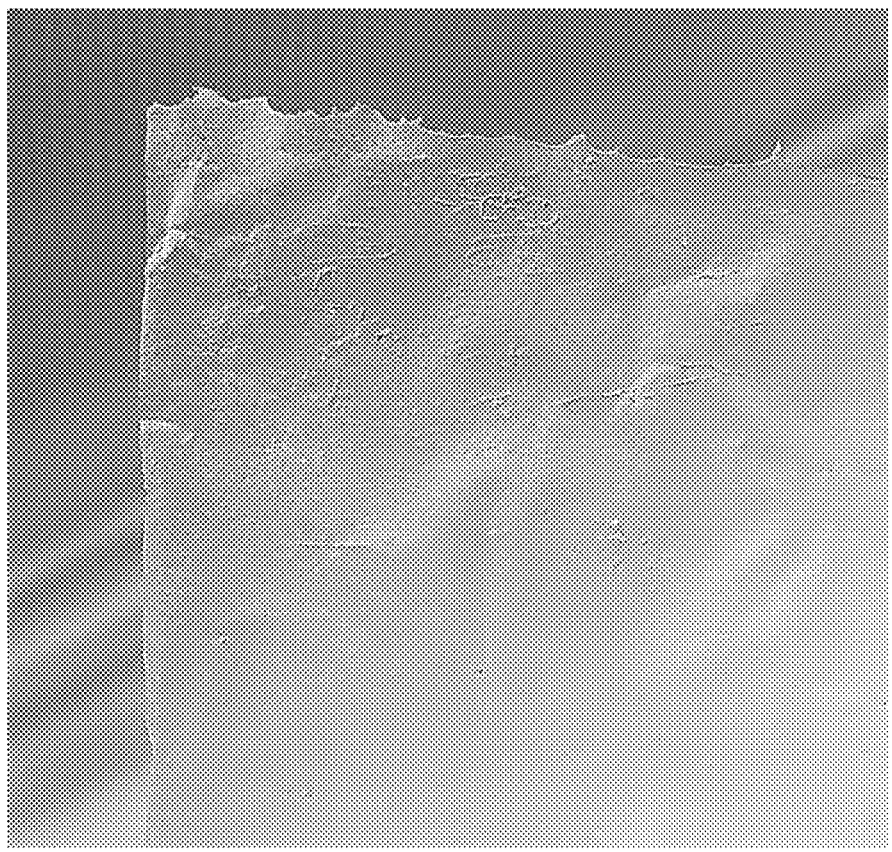
FIG. 8B. Close up view of a hydrogel membrane with embedded amnion tissue in an embodiment.
Figure 9:
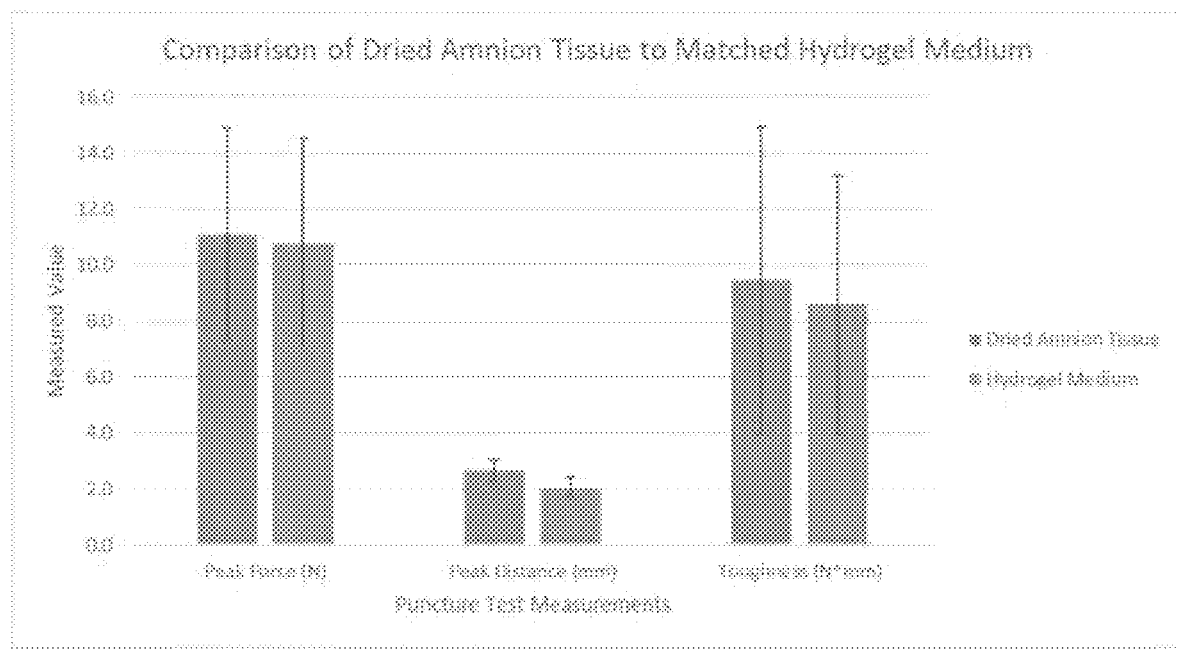
FIG. 9. Comparison of mechanical properties measured via puncture testing of amnion tissue and a matched hydrogel medium in an embodiment.

This example illustrates an embodiment in which the hydrogel medium with embedded amnion tissue is matched to the unprocessed amnion tissue. The hydrogel medium was prepared as described in Example 2 and visually compared to unprocessed donor amnion as well as hydrogel medium without embedded tissue (FIG. 7). The three samples were thin, translucent, and comparable in feel and behavior. The hydrogel medium without embedded tissue was clear and translucent whereas the hydrogel medium with the embedded tissue was granular in appearance due to the presence of the tissue segments (FIG. 8). The mechanical properties of the dried amnion tissue, measured via puncture testing, were matched to the mechanical properties of the hydrogel medium (FIG. 9).

Example 4

Figure 10:
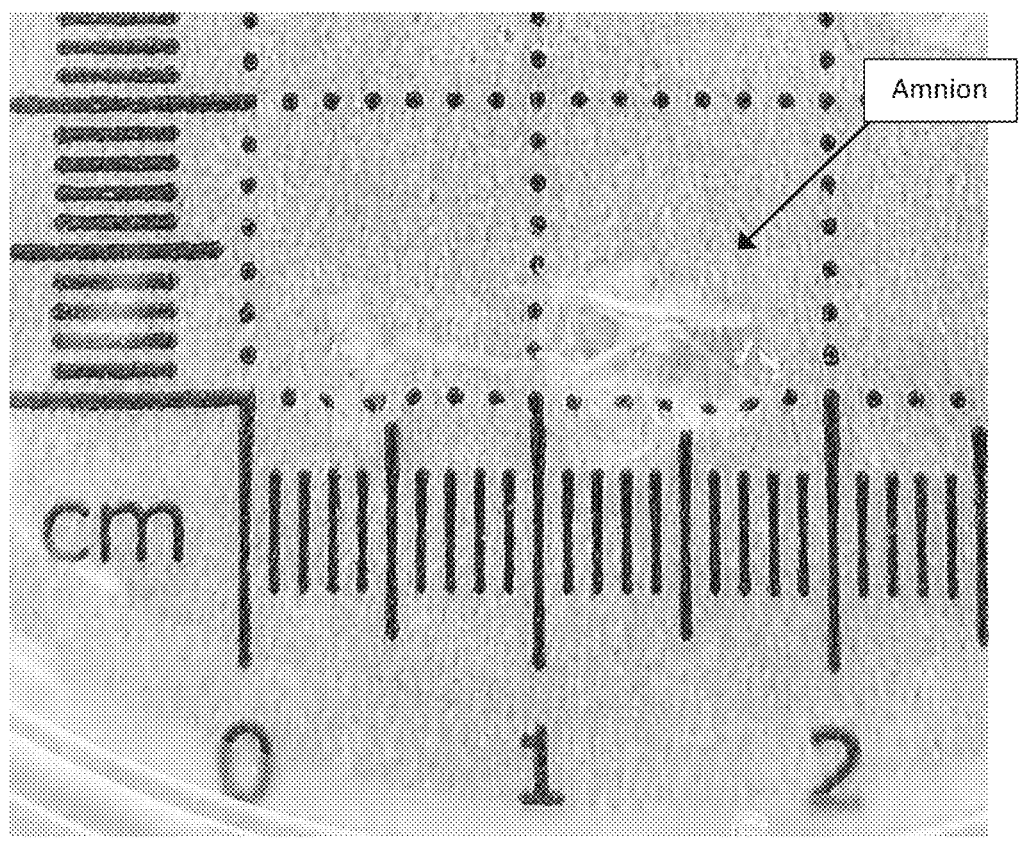
FIG. 10. Released segments of amnion tissue that had been stored and preserved in a hydrogel medium.

This example illustrates an embodiment in which amnion tissue was stored and preserved in a hydrogel medium through transport and storage. A membrane with embedded amnion tissue was prepared as described in Example 2 and then dried, packaged, and transported 600 miles overnight by air. After reaching the destination the membrane was stored refrigerated for 18 days. After storage, the membrane was removed from refrigeration and treated with a liquid stimulus applied evenly to the surface of the membrane. The liquid stimulus disrupted the crosslinks within the alginate component inducing dissolution of the hydrogel medium and release of the embedded tissue segments (FIG. 10).

Example 5

Figure 11A:
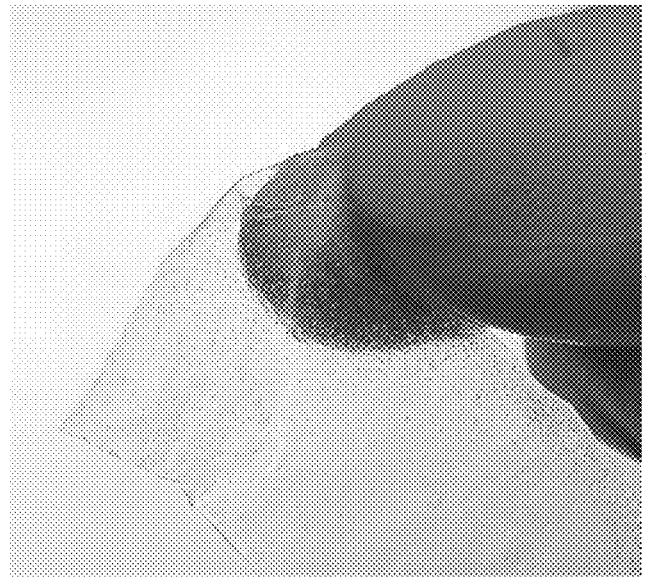
FIG. 11A. A hydrogel membrane that stored embedded amnion tissue for 18 months. The granular appearance of the membrane is due to the presence of the tissue.

This example illustrates an embodiment in which amnion tissue was stored and preserved in a hydrogel medium for 18 months. A membrane with embedded amnion tissue was prepared as described in Example 1 and then stored wet and refrigerated for a period of 18 months. After storage, the membrane was removed from refrigeration and treated with a liquid stimulus applied evenly to the surface of the membrane. The liquid stimulus disrupted the crosslinks within the alginate component inducing dissolution of the hydrogel medium and release of the embedded tissue segments (FIG. 11).

Example 6

This example illustrates an embodiment of a multilayer construct comprising small intestinal submucosa (SIS) (layer #1) and a planar hydrogel medium (layer #2) comprised of alginate and hyaluronate. The multilayer construct was stabilized through crosslinking and dried. The strength of adherence of the two layers (the SIS layer adhering to the hydrogel layer) was challenged after rehydration by extensive manipulation such as rolling, folding, scraping, shearing, and flipping and flinging, before being deployed through a trocar in an abdominal cadaveric surgical model. The hydrogel medium remained adhered to the SIS throughout the manipulations.

Example 7

This example illustrates an embodiment in which amnion tissue is combined with a planar hydrogel medium via pressing. A portion of amnion tissue segments are added to a planar hydrogel medium measuring 2"×2". The hydrogel medium with tissue is then sandwiched with sterile backing material and placed onto the platen of a pneumatic press. The hydrogel medium and tissue are compressed for 15 minutes at 325 lbs. force (lbf) to cause adherence between the hydrogel and tissue. The adherence can be further strengthened by drying the hydrogel/tissue construct (FIG. 12).

Example 8 includes a sheet and a plurality of tissue segments.

In Example 9, the subject matter of Example 8 can optionally include wherein the sheet is comprised of alginate.

In Example 10, the subject matter of Example 8 can optionally include wherein the tissue segments are comprised of amnion, chorion, placenta, or a mixture thereof.

In Example 11, the subject matter of Example 8 can optionally include wherein the average size of the tissue segments is greater than 0.1 mm and less than 10 mm.

In Example 12, the subject matter of Example 8 can optionally include wherein the sheet has a first side and a second side, and the tissue segments are adhered to the first side.

In Example 13, the subject matter of Example 8 can optionally include wherein the sheet has a width and a length, and the width is at least 0.5 inches and the length is at least 0.5 inches.

In Example 14, the subject matter of Example 8 can optionally include wherein the sheet is a hydrogel.

In Example 15, the subject matter of Example 8 can optionally include wherein the sheet has a first side and a second side, and the surface area of each of the sides is at least 50 in$^2$.

In Example 16, the subject matter if Example 9 can optionally include wherein the sheet is further comprised of hyaluronate.

In Example 17, the subject matter of Example 16 can optionally include wherein the hyaluronate is uncrosslinked; the alginate is crosslinked; and the alginate is crosslinked around the uncrosslinked hyaluronate.

In Example 18, the subject matter of Example 17 can optionally include wherein the alginate is crosslinked with calcium.

In Example 19, the subject matter of Example 12 can optionally include wherein the tissue segments are further adhered to the second side.

Example 20 includes a method comprising the steps of using a hydrogel medium as a preservation agent for a tissue, wherein the preservation agent preserves the extracellular matrix of the tissue.

In Example 21, the subject matter of Example 20 can optionally include wherein the extracellular matrix comprises collagen.

In Example 22, the subject matter of Example 20 can optionally include wherein the tissue is comprised of amnion, chorion, placenta, or a mixture thereof.

Example 23 includes a method of using a hydrogel medium as a storage agent for a tissue.

In Example 24, the subject matter of Example 23 can optionally include wherein the tissue is embedded in the hydrogel medium and remains embedded through processing, transport, and storage.

In Example 25, the subject matter of Example 23 can optionally include wherein the tissue is adhered to the hydrogel medium and remains adhered to the tissue hydrogel medium through processing, transport, and storage.

Example 26 includes a method comprising the steps of combining a tissue with a hydrogel medium for processing, transport, and storage; using the hydrogel medium and tissue to cover and protect an injury site; treating the hydrogel medium with a stimulus that releases the tissue from the hydrogel medium such that the tissue is introduced to the injury site.

Example 27 includes a kit comprising a hydrogel sheet and a solution; wherein the hydrogel sheet has a first side and a second side; wherein a plurality of amnion tissue segments are adhered to the first side; wherein the solution is comprised of water and citrate salt; wherein the hydrogel sheet is comprised of alginate and hyaluronate.

Example 28 includes the kit of example 27 wherein the hydrogel sheet is imprinted with a cross-hatch pattern.

Example 29 includes a composition comprising a dry sheet and a plurality of amnion tissue segments; wherein the hydrogel sheet has a first side and a second side; wherein the plurality of amnion tissue segments are adhered to the first side; wherein the average size of the segments ranges from 0.5 mm to 1.2 mm; wherein the sheet is comprised of alginate and hyaluronate;

wherein the hyaluronate is uncrosslinked, the alginate is crosslinked, and the alginate is crosslinked around the hyaluronate; wherein the alginate is crosslinked with calcium; wherein the sheet has a width, a length, and a thickness; wherein each side of the sheet possesses 4 square inches of surface area; wherein the width and length are greater than the thickness; wherein the sheet is imprinted with a cross-hatch pattern; wherein the sheet is translucent.

In an embodiment, tissue segments may be adhered to a hydrogel surface in a gradient form. A gradient may direct cellular migration. For example, see FIG. 1B.

Example 1a

An apparatus comprising: a hydrogel film including: (a)(i) an upper surface having a width and a length, (a)(ii) a lower surface having a width and a length, (a)(iii) sidewalls that respectively couple the widths and lengths of the upper and lower surfaces to each other;

first and second segments of non-viable extracellular matrix; wherein (b)(i) each of the first and second segments is substantially planar, (b)(ii) each of the first and second segments includes an upper surface and a lower surface, (b)(iii) each upper surface of the first and second segments is between 0.1 mm$^2$ to 5 mm$^2$ in area; wherein (c)(i) a portion of each of the first and second segments emerges from the upper surface of the hydrogel film, (c)(ii) an additional portion of each of the first and second segments is submerged within the hydrogel film and between the upper and lower surfaces of the hydrogel film; wherein a height of the sidewalls is less than 2 mm, the height being measured orthogonal to the length and width of the upper surface.

Figure 1E:
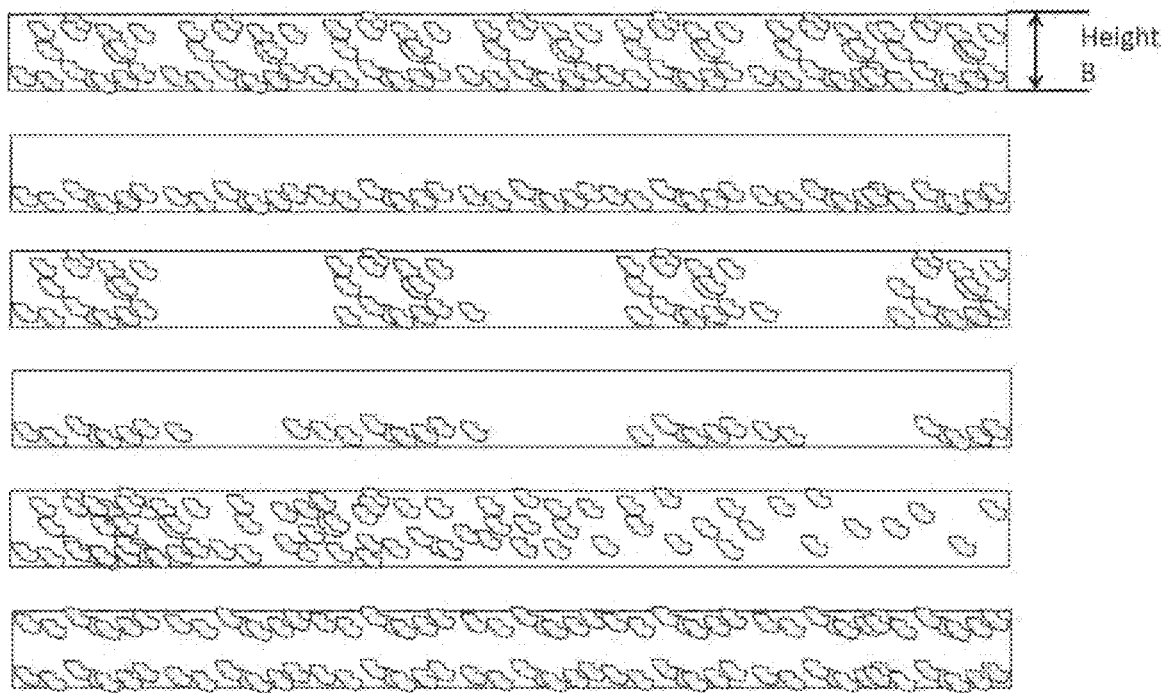
FIG. 1E. Profile view of various spatial arrangements of tissue pieces embedded in the hydrogel medium in an embodiment.

For instance, see FIG. 1E.

In other embodiments the height of the sidewalls is less than 1, 3, 4, or 5 mm.

A height of 2 mm or less can be critical in some embodiments. For example, for handling (such that a film can be rolled and inserted into a patient via a trocar) the thickness may be a critical limiting factor. Further, the size of tissue may be critical. For example, for embodiments where powder is not desirable for whatever reason, the tissue may be sized as indicated directly above. This presents issues when forming a hydrogel. For example, vortexing large tissue segments in a hydrogel and then turning that gel into a film can be problematic in that the segments may tear the film or be clumped within the film (due to dragging of the tissue when the film is made) thereby decreasing the effective surface area of the tissues. Also, manufacturing a film instead of a bulk hydrogel poses different issues for coupling such a hydrogel to relatively larger tissue segments (e.g., using a doctor blade to form a 1 mm hydrogel poses different issues than forming a 10 mm thick bulk hydrogel due to the pulling of the doctor blade over the tissue segments).

Example 1a'

An apparatus comprising: a hydrogel film including: (a)(i) an upper surface having a width and a length, (a)(ii) a lower surface having a width and a length, (a)(iii) sidewalls that respectively couple the widths and lengths of the upper and lower surfaces to each other;

first and second segments of tissue; wherein (b)(i) each of the first and second segments is substantially planar, (b)(ii) each of the first and second segments includes an upper surface and a lower surface, (b)(iii) each upper surface of the first and second segments is between 0.1 mm² to 5 mm² in area; wherein (c)(i) a portion of each of the first and second segments emerges from the upper surface of the hydrogel film, (c)(ii) an additional portion of each of the first and second segments is submerged within the hydrogel film and between the upper and lower surfaces of the hydrogel film; wherein a height of the sidewalls is less than 2 mm, the height being measured orthogonal to the length and width of the upper surface.

Example 1a''

An apparatus comprising: a hydrogel film including: (a)(i) an upper surface having a width and a length, (a)(ii) a lower surface having a width and a length, (a)(iii) sidewalls that respectively couple the widths and lengths of the upper and lower surfaces to each other;

first and second segments of tissue; wherein each of the first and second segments is between 0.1 mm² to 5 mm² in area; wherein (b)(i) a portion of each of the first and second segments emerges from the upper surface of the hydrogel film, (b)(ii) an additional portion of each of the first and second segments is submerged within the hydrogel film and between the upper and lower surfaces of the hydrogel film; wherein a height of the sidewalls is less than 2 mm, the height being measured orthogonal to the length and width of the upper surface.

Example 1a'''

An apparatus comprising: a hydrogel film including: (a)(i) an upper surface having a width and a length, (a)(ii) a lower surface having a width and a length, (a)(iii) sidewalls that respectively couple the widths and lengths of the upper and lower surfaces to each other;

first and second segments of tissue; wherein (b)(i) a portion of each of the first and second segments emerges from the upper surface of the hydrogel film, (b)(ii) an additional portion of each of the first and second segments is submerged within the hydrogel film and between the upper and lower surfaces of the hydrogel film; wherein a height of the sidewalls is less than 2 mm, the height being measured orthogonal to the length and width of the upper surface.

Example 2a

The apparatus of example 1a, wherein: the upper surface of the hydrogel film includes an impression; the impression includes additional sidewalls that are not parallel to the upper surface; the sidewalls do not contact the first and second segments; the sidewalls do not contact the additional sidewalls.

In an embodiment, the membranes can be obtained by pressing tissue or tissue segments onto the surface of a polymer membrane, for example via pneumatic press or hydraulic press, to adhere the tissue or tissue segments to the membrane without encapsulation of the tissue.

For instance, see FIG. 12.

Example 3a

The apparatus of example 2a, wherein: the sidewalls define a first series of substantially parallel lines; the sidewalls define a second series of substantially parallel lines; the first and second series of substantially parallel lines intersect one another.

For instance, see FIG. 12. Many substrates may impose such a pattern. For example, a pattern of evenly spaced dots produces such intersecting lines. A substrate with such a pattern may provide air space between portions of the substrate (e.g., fabric portions of gauze) that helps the hydrogel not adhere to platens or plates that are used to press the hydrogel in order to adhere the tissue to the hydrogel.

Example 4a

The apparatus of example 2a, wherein the hydrogel film is substantially planar.

Example 5a

The apparatus of example 4a, wherein the hydrogel film is substantially dry but not desiccated.

Example 6a

The apparatus of example 1a, wherein: the upper surface of the hydrogel film includes troughs that collectively form a mesh pattern; the mesh pattern covers a majority of the upper surface of the hydrogel film.

For instance, see FIG. 12. Gauze is just one example of a substrate that may impart such a pattern onto a hydrogel.

The mesh pattern may show lines or other structures intersecting one another.

Example 7a

The apparatus of example 6a, wherein: the lower surface of the hydrogel film includes troughs that collectively form a mesh pattern; the mesh pattern covers a majority of the lower surface of the hydrogel film.

For instance, gauze may be used on both sides of the hydrogel (i.e., to sandwich the hydrogel between gauze portions) to keep either side of the hydrogel from adhering to any portion of a hydraulic press system.

Example 8a

The apparatus of example 1a comprising: uncrosslinked hyaluronic acid included in the hydrogel; and crosslinked alginate included in the hydrogel; wherein: the alginate is crosslinked with calcium; the alginate is crosslinked around the uncrosslinked hyaluronic acid to retain the uncrosslinked hyaluronic acid within the alginate.

Example 9a

The apparatus of example 8a included in a kit comprising a calcium chelator.

Figure 11B:
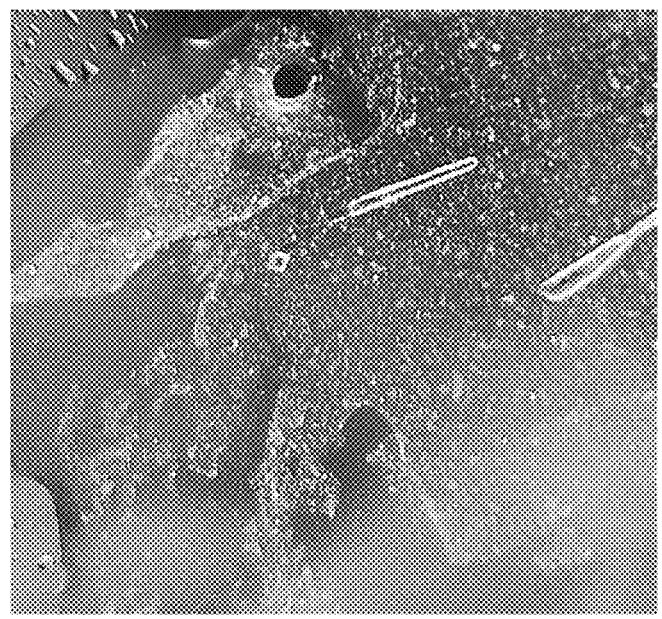
FIG. 11B. The hydrogel of FIG. 11A after treatment with a liquid stimulus to dissolve the hydrogel medium and release the granular tissue segments.

Such a chelator constitutes a liquid stimulus of FIG. 11B.

Example 10a

The apparatus of example 8a, wherein the hydrogel film consists essentially of the uncrosslinked hyaluronic acid and the crosslinked alginate.

This pertains to the hydrogel itself. For instance, in this example the tissue segments are additives to the hydrogel but the hydrogel itself includes only hyaluronic acid and alginate.

Example 11a

The apparatus of example 8a, wherein the alginate is crosslinked with a calcium-based salt.

Example 12a

The apparatus of example 8a, wherein the alginate is crosslinked around the first and second segments to retain the first and second segments within the alginate.

For instance, the tissue segments can be spread onto a flat substrate and then the casting solution can be spread over top of the tissue segments using a suitable film applicator to yield a membrane in which the tissue is present on only the membrane's bottom surface. Afterword, crosslinking can occur to crosslink the alginate around the segment to retain the segments within the hydrogel.

Crosslinking may occur after (or before) pressing (e.g., with a hydraulic press) occurs, so having the tissue segments retained within a hydrogel via crosslinking is not exclusive or pressing or any many other embodiments described herein.

Example 13a

The apparatus of example 1a comprising alginate, wherein the first and second segments are physically constrained within the hydrogel film in response to the alginate being crosslinked around the first and second segments.

For instance, the tissue segments can be spread onto a flat substrate and then the casting solution can be spread over top of the tissue segments using a suitable film applicator to yield a membrane in which the tissue is present on only the membrane's bottom surface. Afterword, crosslinking can occur to crosslink the alginate around the segment to retain the segments within the hydrogel.

This is not to say that the tissue is not also restrained within the hydrogel due to the tissue being pressed into the hydrogel via a hydraulic press and the like.

For embodiments that include compression, crosslinking may occur before or after the compression.

Example 14a

The apparatus of example 13a comprising carboxymethylcellulose, wherein the carboxymethylcellulose is physically constrained within the hydrogel film in response to the alginate being crosslinked around the carboxymethylcellulose.

Example 15a

The apparatus of example 1a comprising: third and fourth segments of non-viable extracellular matrix; wherein (a)(i) each of the third and fourth segments is substantially planar, (b)(ii) each of the third and fourth segments includes an upper surface and a lower surface, (b)(iii) each upper surface of the third and fourth segments is between 0.1 mm$^2$ to 5 mm$^2$ in area; wherein (c)(i) a portion of each of the third and fourth segments emerges from the lower surface of the hydrogel film, (c)(ii) an additional portion of each of the third and fourth segments is submerged within the hydrogel film and between the upper and lower surfaces of the hydrogel film; wherein no portion of the first and second segments emerges from the lower surface of the hydrogel film; wherein no portion of the third and fourth segments emerges from the upper surface of the hydrogel film.

For instance, see the bottom panel of FIG. 1E.

Example 15a'

The apparatus of example 1a comprising: third and fourth segments of non-viable extracellular matrix; wherein (a)(i) each of the third and fourth segments is substantially planar, (b)(ii) each of the third and fourth segments includes an upper surface and a lower surface, (b)(iii) each upper surface of the third and fourth segments is between 0.1 mm$^2$ to 5 mm$^2$ in area; wherein (c)(i) a portion of each of the third and fourth segments emerges from the lower surface of the hydrogel film, (c)(ii) an additional portion of each of the third and fourth segments is submerged within the hydrogel film and between the upper and lower surfaces of the hydrogel film.

Example 16a

The apparatus of example 1a, wherein another portion of each of the first and second segments emerges from the lower surface of the hydrogel film.

Thus, in some embodiment the segment traverses the entire film. This may occur with an extremely thin film (e.g., less than 1 or 2 mm in thickness) with a tissue segment greater than 1 or 2 mm in length.

Example 17a

The apparatus of example 1a, wherein the width and length of the upper surface are both at least 0.5 inches.

In other embodiments the width and length of the upper surface are both at least 0.25, 0.75, 1.00, 1.25, 1.50, 1.75, 2.0, 3.0, 4.0 or more inches.

Example 18a

The apparatus of example 1a, wherein: a portion of the hydrogel film is included between the first and second segments; the portion does not include the first and second segments and includes no additional segments of non-viable extracellular matrix; the portion contacts the upper and lower surfaces of the hydrogel film; the portion includes a substantially consistent density from upper surfaces of the hydrogel film to the lower surface of the hydrogel film.

Example 18a'

The apparatus of example 1a, wherein: a portion of the hydrogel film is included between the first and second segments but does not contact the first and second segments or any other segments of non-viable extracellular matrix; the portion contacts the upper and lower surfaces of the hydrogel film; the portion includes a substantially consistent density from upper surfaces of the hydrogel film to the lower surface of the hydrogel film.

Such a consistent density may be due to, for instance, hydraulic or pneumatic pressing.

Example 19a

A method comprising: preparing an aqueous mixture of alginate and hyaluronic acid; crosslinking the alginate around the hyaluronic acid to form a hydrogel film, the hydrogel film including: (a)(i) an upper surface having a width and a length, (a)(ii) a lower surface having a width and a length, (a)(iii) sidewalls that respectively couple the widths and lengths of the upper and lower surfaces to each other; contacting an upper surface of the hydrogel film with first and second segments of non-viable extracellular matrix; wherein (b)(i) each of the first and second segments is substantially planar, (b)(ii) each of the first and second segments includes an upper surface and a lower surface, (b)(iii) each upper surface of the first and second segments is between 0.1 mm$^2$ to 5 mm$^2$ in area; coupling a substrate to the upper surface of the hydrogel film and to the first and second segments; pressing the substrate towards the upper of surface of the hydrogel film with a force of at least 150 pounds force (lbf);

in response to pressing the substrate towards the upper of surface of the hydrogel film, (c)(i) impressing the first and second segments into the hydrogel film such that a portion of each of the first and second segments emerges from the upper surface of the hydrogel film, and (c)(ii) an additional portion of each of the first and second segments is submerged within the hydrogel film and between the upper and lower surfaces of the hydrogel film.

Example 19a'

A method comprising: preparing an aqueous mixture of alginate and hyaluronic acid; contacting an upper surface of the mixture with first and second segments of non-viable extracellular matrix; crosslinking the alginate around the hyaluronic acid and the first and second segments to form a hydrogel film, the hydrogel film including: (a)(i) an upper surface having a width and a length, (a)(ii) a lower surface having a width and a length, (a)(iii) sidewalls that respectively couple the widths and lengths of the upper and lower surfaces to each other;

wherein (b)(i) each of the first and second segments is substantially planar, (b)(ii) each of the first and second segments includes an upper surface and a lower surface, (b)(iii) each upper surface of the first and second segments is between 0.1 mm$^2$ to 5 mm$^2$ in area; wherein in response to contacting an upper surface of the mixture with first and second segments of non-viable extracellular matrix, (c)(i) a portion of each of the first and second segments emerges from the upper surface of the hydrogel film, and (c)(ii) an additional portion of each of the first and second segments is submerged within the hydrogel film and between the upper and lower surfaces of the hydrogel film.

Example 20a

The method of example 19a comprising: in response to pressing the substrate towards the upper of surface of the hydrogel film, forming a pattern on the upper surface of the hydrogel film; wherein the pattern corresponds to a pattern on the substrate.

Example 21a

The apparatus of example 1a, wherein: segments of non-viable extracellular matrix are not evenly distributed throughout the hydrogel film; segments of non-viable extracellular matrix, which do not emerge from the upper or lower surfaces of the hydrogel film, are absent from a central core area of the hydrogel film; the central core area includes a middle third of the hydrogel film measured parallel to the height of the hydrogel film; the central core area includes a middle third of the hydrogel film measured parallel to the length of the hydrogel film.

For example, generally see the bottom panel of FIG. 1E.

The foregoing description of the embodiments has been presented for the purposes of illustration and description. It is not intended to be exhaustive or to limit the embodiments to the precise forms disclosed. This description and the claims following include terms, such as left, right, top, bottom, over, under, upper, lower, first, second, etc. that are used for descriptive purposes only and are not to be construed as limiting. For example, terms designating relative vertical position refer to a situation where an active surface of a substrate is the "top" surface of that substrate; the substrate may actually be in any orientation so that a "top" side of a substrate may be lower than the "bottom" side in a standard terrestrial frame of reference and still fall within the meaning of the term "top." The term "on" as used herein (including in the claims) does not indicate that a first layer "on" a second layer is directly on and in immediate contact with the second layer unless such is specifically stated; there may be a third layer or other structure between the first layer and the second layer on the first layer. The embodiments of a device or article described herein can be manufactured, used, or shipped in a number of positions and orientations. Persons skilled in the relevant art can appreciate that many modifications and variations are possible in light of the above teaching. Persons skilled in the art will recognize various equivalent combinations and substitutions for various components shown in the Figures. It is therefore intended that the scope of the invention be limited not by this detailed description, but rather by the claims appended hereto.

What is claimed is:

1. An apparatus comprising:
    a hydrogel including: (a) (i) an upper surface having a width and a length, (a) (ii) a lower surface having a width and a length, (a) (iii) sidewalls that respectively couple the widths and lengths of the upper and lower surfaces to each other;
    first, second, third, and fourth segments of non-viable extracellular matrix;
    wherein (b) (i) a portion of each of the first and second segments emerges from the upper surface of the hydrogel and a portion of each of the third and fourth segments emerges from the lower surface of the hydrogel, (b) (ii) an additional portion of each of the first, second, third, and fourth segments is submerged within the hydrogel and between the upper and lower surfaces of the hydrogel;
    wherein no portion of the first or second segments emerges from the lower surface of the hydrogel and no portion of the third or fourth segments emerges from the upper surface of the hydrogel;
    wherein the hydrogel includes hyaluronic acid and alginate.

2. The apparatus of claim 1, wherein:
    the upper surface of the hydrogel includes troughs that collectively form a mesh pattern;
    the mesh pattern covers a majority of the upper surface of the hydrogel.

3. The apparatus of claim 1 wherein:
    the hyaluronic acid is uncrosslinked;
    at least a portion of the alginate is crosslinked with calcium;

the alginate is crosslinked around the uncrosslinked hyaluronic acid to retain the uncrosslinked hyaluronic acid within the alginate.

4. The apparatus of claim 3 included in a kit comprising a calcium chelator.

5. The apparatus of claim 1, wherein:
the alginate is crosslinked around the first and second segments;
the first and second segments are physically constrained within the hydrogel in response to the alginate being crosslinked around the first and second segments.

6. The apparatus of claim 5 comprising carboxymethylcellulose, wherein the carboxymethylcellulose is physically constrained within the hydrogel in response to the alginate being crosslinked around the carboxymethylcellulose.

7. The apparatus of claim 1, wherein:
a portion of the hydrogel is included between the first and second segments;
the portion does not include the first and second segments and includes no additional segments of non-viable extracellular matrix;
the portion contacts the upper and lower surfaces of the hydrogel.

8. The apparatus of claim 7, wherein the portion includes a consistent density from the upper surface of the hydrogel to the lower surface of the hydrogel.

9. The apparatus of claim 1, wherein:
segments of non-viable extracellular matrix are not evenly distributed throughout the hydrogel;
segments of non-viable extracellular matrix, which do not emerge from the upper or lower surfaces of the hydrogel, are absent from a central core area of the hydrogel;
the central core area includes a middle third of the hydrogel measured parallel to a height of the hydrogel;
the central core area includes a middle third of the hydrogel measured parallel to the length of the hydrogel.

10. The apparatus of claim 1 comprising:
fifth and sixth segments of non-viable extracellular matrix;
wherein no portion of the fifth or sixth segments emerges from the lower surface of the hydrogel;
wherein no portion of the fifth or sixth segments emerges from the upper surface of the hydrogel.

11. An apparatus comprising:
a hydrogel including: (a) (i) an upper surface having a width and a length, (a) (ii) a lower surface having a width and a length, (a) (iii) sidewalls that respectively couple the widths and lengths of the upper and lower surfaces to each other;
first, second, third, and fourth segments of non-viable extracellular matrix;
wherein (b) (i) a portion of each of the first and second segments emerges from the upper surface of the hydrogel, (b) (ii) an additional portion of each of the first and second segments is submerged within the hydrogel and between the upper and lower surfaces of the hydrogel;
wherein no portion of the first or second segments emerges from the lower surface of the hydrogel;
wherein no portion of the third or fourth segments emerges from the lower surface of the hydrogel;
wherein no portion of the third or fourth segments emerges from the upper surface of the hydrogel;
wherein the hydrogel includes hyaluronic acid and alginate.

12. The apparatus of claim 11, wherein:
the upper surface of the hydrogel includes troughs that collectively form a mesh pattern;
the mesh pattern covers a majority of the upper surface of the hydrogel.

13. The apparatus of claim 11 wherein:
the hyaluronic acid is uncrosslinked;
at least a portion of the alginate is crosslinked with calcium;
the alginate is crosslinked around the uncrosslinked hyaluronic acid to retain the uncrosslinked hyaluronic acid within the alginate.

14. The apparatus of claim 13 included in a kit comprising a calcium chelator.

15. The apparatus of claim 11, wherein:
the alginate is crosslinked around the first and second segments;
the first and second segments are physically constrained within the hydrogel in response to the alginate being crosslinked around the first and second segments.

16. The apparatus of claim 15 comprising carboxymethylcellulose, wherein the carboxymethylcellulose is physically constrained within the hydrogel in response to the alginate being crosslinked around the carboxymethylcellulose.

17. The apparatus of claim 11, wherein:
a portion of the hydrogel is included between the first and second segments;
the portion does not include the first and second segments and includes no additional segments of non-viable extracellular matrix;
the portion contacts the upper and lower surfaces of the hydrogel.

18. The apparatus of claim 17, wherein the portion includes a consistent density from the upper surface of the hydrogel to the lower surface of the hydrogel.

19. The apparatus of claim 11, wherein:
segments of non-viable extracellular matrix are not evenly distributed throughout the hydrogel;
segments of non-viable extracellular matrix, which do not emerge from the upper or lower surfaces of the hydrogel, are absent from a central core area of the hydrogel;
the central core area includes a middle third of the hydrogel measured parallel to a height of the hydrogel;
the central core area includes a middle third of the hydrogel measured parallel to the length of the hydrogel.

* * * * *